Figure 1A:
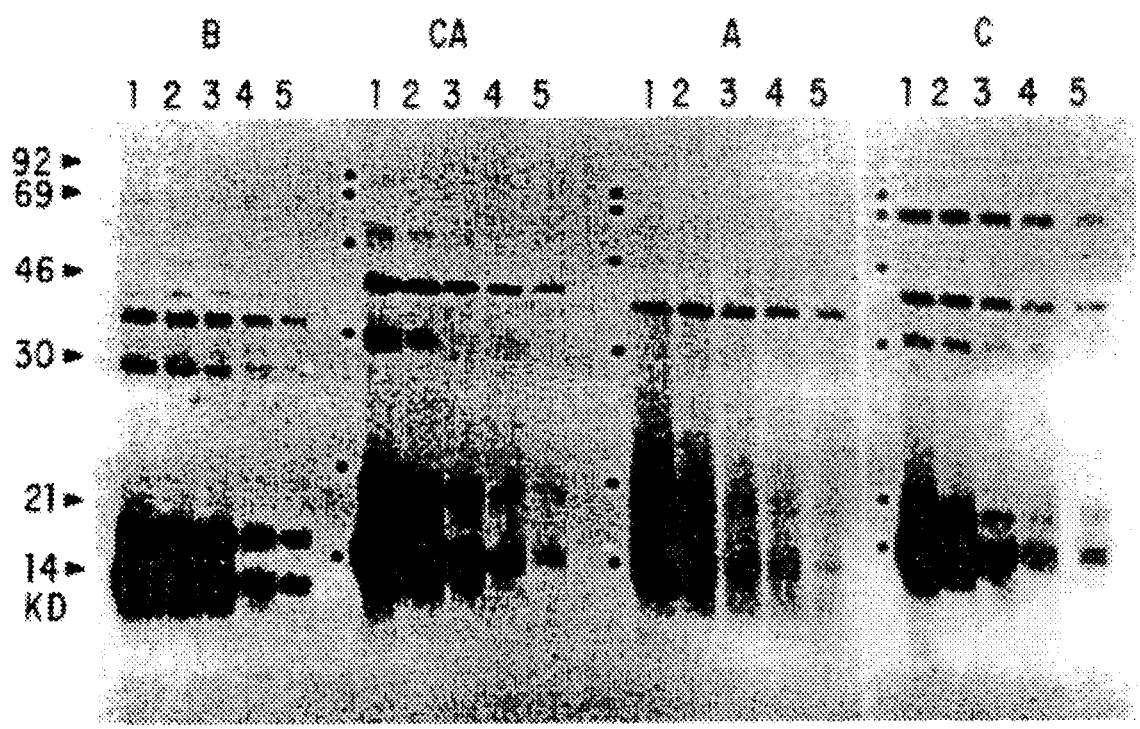

United States Patent [19]
Valenta et al.

[11] Patent Number: 5,648,242
[45] Date of Patent: Jul. 15, 1997

[54] METHOD OF PRODUCTION OF BIRCH POLLEN ALLERGEN P14

[75] Inventors: Rudolf Valenta, Theresienfeld; Michael Duchene, Vienna; Karin Pettenburger, Vienna; Michael Breitenbach, Vienna; Dietrich Kraft, Vienna; Helmut Rumpold, Vienna; Otto Scheiner, Mariaenzersdorf, all of Austria

[73] Assignee: Biomay Produktions - Und Handelsgesellschaft M.B.H., Linz, Austria

[21] Appl. No.: 469,555

[22] Filed: Jun. 6, 1995

Related U.S. Application Data

[60] Division of Ser. No. 846,992, Jun. 6, 1992, which is a continuation-in-part of Ser. No. 683,832, Apr. 11, 1991, abandoned.

[30] Foreign Application Priority Data

Aug. 13, 1990 [AU] Australia ................... 1685/90

[51] Int. Cl.⁶ ............................ C12P 21/06; C07H 21/04
[52] U.S. Cl. .................... 435/69.3; 435/69.1; 536/23.1; 536/23.6
[58] Field of Search .................. 435/91.1, 91.51, 435/91.4, 320.1, 69.1, 69.3; 536/23.6, 23.1

[56] References Cited

U.S. PATENT DOCUMENTS 4,721,668  1/1988  Jones, III et al. ................... 435/6

FOREIGN PATENT DOCUMENTS

| | | |
|---|---|---|
| A3147763 | 6/1983 | Germany. |
| WO89/09260 | 10/1989 | WIPO. |
| WO90/11293 | 10/1990 | WIPO. |

OTHER PUBLICATIONS

Clinical Experimental Allergy, vol. 20, 1990, Suppl. 1, Meeting 8–11 Jul. 1990, S. d'Abusco et al.: "Characterization of cDNA for Parietaria pollen allergens", p. 48, see abstract OP52.

Biochimica et Biophysica Acta, vol. 967, 1988, Elsevier, U. Lindberg et al.: "The use of poly(L–proline)–sepharose in the isolation of prolifin and profilactin complexes", pp. 391–400.

Int. Arch. Allergy Appl. Immunol., vol. 87, 1988, H. Breiteneder et al.: "Isolation and characterization of messenger RNA from male inflorescences and pollen of the white birch (*Betula verrucosa*), pp. 19–24, see p. 21, left–hand column, 37 Immunoblotting of aqueous BV pollen extracts".

Science, vol. 253, 2 Aug. 1991, R. Valenta et al.: "Identification of profilin as a novel pollen allergen; IgE autoreactivty in sensitized individuals", pp. 557–560.

The EMBO Journal, vol. 8, No. 7, Jul. 1989, (Eynsham, Oxford GB) H. Breiteneder et al.: "The gene coding for the major birch pollen allergen Betv1, is highly homologous to a pea disease resistance response gene", pp. 1935–1938.

Allergy, vol. 44, No. 6, Aug. 1989, E. Jarolim et al.: "IgE and IgG antibodies of patients with allergy to birch pollen as tools to define the allergen profile of *Betula verrucosa*", pp. 385–395.

Allergy, vol. 45, No. 6, Aug. 1990, T. Birner et al.: "Evaluation of immunotherapy–induced changes in specific IgE, IgG and IgG subclasses in birch pollen allergic patients by means of immunoblotting", pp. 418–426.

Chemical Abstracts, vol. 97:53816e "Comparative studies on tree pollen allergens. IV. Evaluation of two commercially avaiable allergen extracts of alder (*Alnus incana*) and birch (*Betula verrucosa*) pollen", 1982, p. 480.

Chemical Abstracts, vol. 104:184481c "Comparative studies on tree pollen allergens. XIII. Partial characterization of the alder (*Alnus incana*) pollen extract by two–dimensional IEF/SDS–PAG electrophoresis combined with electrophoretic transfer and immunoautoradiography", 1986.

Chemical Abstracts, vol. 104:18392e "Immunochemical characterization of reference alder (*Alnus glutinosa*) and hazel (*Corylus avellana*) pollen extracts and the partial immunochemical identity between the major allergens of alder, birch and hazel pollens" 1986, p. 380.

Chemical Abstracts, vol. 107:234414t "Allergologic–immunochemical investigation of various tree pollens. Part I—Characterization of antigen and allergen components in birch, beech, alder, hazel and oak pollens", 1987.

Ipsen, H. and Hansen, O.C. In: *Epitopes of Atopic Allergens*. Sehon, A.H., kraft, D., Kunkel, G. (eds) (1990) UCB, Brussels, Belgium, pp. 3–8.

Rumpold, et al. In: *Epitopes of Atopic Allergens*. Sehon, A.H., Kraft, D., Kunkel, G. (eds) (1990) UCB, Brussels, Belgium, pp. 26–28.

Valenta, et al. In: *Epitopes of Atopic Allergens*. Sehon, A. H., Kraft, D., Kunkel, G. (eds) (1990) UCB Brussels, Belgium, pp. 73–76.

Florvaag, E. et al. Int. Arch. Allergy Appl. Immunol. 75:300–308 (1984).

Florvaag, E. et al. Int. Arch, Allergy Appl. Immunol. 67:49–56 (1982).

Jarolim, et al. Int. Arch. Allergy Appl Immunol. 90:54–60 (1989).

(List continued on next page.)

*Primary Examiner*—Christina Y. Chan
*Assistant Examiner*—Patrick J. Nolan
*Attorney, Agent, or Firm*—Pennie & Edmonds

[57] ABSTRACT

The invention provides recombinant DNA molecules which code for polypeptides that exhibit the antigenicity of a P14 allergen of birch *Betula verrucosa* and other plants of the order Fagales, and for polypeptides comprising at least one epitope thereof, as well as nucleic acids which under stringent conditions hybridize with such DNA sequences or are derivable from such sequences by degeneracy of the genetic code. A method is provided that permits purification of P14 allergens or cross reactive allergens by means of binding to poly(L-proline). In addition, methods are described for making the proteins and polypeptides coded by these DNA molecules and their use in the diagnosis or therapy of diseases.

2 Claims, 18 Drawing Sheets

OTHER PUBLICATIONS

Hatton, T. W., Hill, R.D., Ekramoddoullah, A.K.M., Kisil, F.T. and Sehon, A.H., "Molecular Cloning of Kentucky Bluegrass (KBF) Pollen Allergens," J. Allergy Clin. Immunol., (Jan. 1988) 81(1), Zusammenfassung [Abstract] Nr. 58, siehe den ganzen Artikel, Seite [page] 183.

Lütck, H.a. et al. EMBO J. 6(1):43–48 (1987).

Thomas et al. In: *Epitopes of Atopic Allergens*. Sehon, A.H., Kraft, D., and Kunkel, G. (eds), 1990. UCB Institute of Allergy, Brussels.

Nagai, K. et al. Nature 309:810–812 (1987).

Stinson, J.R. et al. Plant Physiol. 83:442–447 (1987).

Walter, M.H. et al., Proc. Natl. Acad. Sci. USA 85:5546–5550 (Aug. 1988).

Valenta, R. et al. J. Allergy Clin. Immunol. 88(6):889–894 (1991).

Tchang et al. J. Biol. Chem. 263(32):16849–16855 (1988).

Crawford et al. Proc. Natl. Acad. Sci. USA 83:8073–8076 (1986).

Scioli et al. Proc. Natl. Acad. Sci. USA 85:7661–7665 (1988).

Hemmens et al., "A Comparison of the Antigenic and Allergenic Components of Birch and Alder Pollens in Scandinavia and Australia", Int. Archs Allergy Appl. Immun. 85:27–37 (1988).

Berger et al. (eds.) "Molecular Cloning Manual" Methods in Enzymology vol. 152, pp. 316–337, 343–349, 359–371, 451–469 (1987).

Halpern, "In Vitro Diagnosis in Asthma: The State-of-the-Art", Allerg. Immunol. (Paris) 1991, 23(6):255–262.

Harris Hosen, M.D., *Clinical Allergy Based on Provacative Testing*, Explosion Press, Hicksville, New York, e.g., pp. 11–29, (1978).

Oreste et al., "Purification and Characterization of Par o I, Major Antigen of *Pariertaria officinalis* Pollen", Int Arch Appl Immuno 96:19–27 (1991).

Geraci et al., "EMBL/Gen Bank/DDBJ Data Bases *Parietaria judaica* cDNA of Par I", (1994).

```
             10        20        30        40        50        60
CAGAGAAAGCGAAAGCTCTCCGCCACAACAAAACGAAGTAGAAGAAGAAGAGTGAGCAAG
             70        79
AGACAGAGGGAAGAGGAAA
                   90        100       110       120
          ATG TCG TGG CAA ACG TAC GTG GAT GAA CAT TTG ATG TGC GAT ATC
          met ser trp gln thr tyr val asp glu his leu met cys asp ile
             130       140       150       160
          GAC GGG CAA GCC AGC AAC TCG CTG GCA TCT GCG ATC GTC GGT CAC
          asp gly gln ala ser asn ser leu ala ser ala ile val gly his
                   180       190       200       210
          GAT GGC TCT GTG TGG GCC CAG AGC TCT TCC TTC CCA CAG TTT AAG
          asp gly ser val trp ala gln ser ser ser phe pro gln phe lys
             220       230       240       250
          CCT CAG GAA ATC ACT GGT ATC ATG AAG GAC TTT GAG GAG CCG GGT
          pro gln glu ile thr gly ile met lys asp phe glu glu pro gly
                   270       280       290       300
          CAT CTT GCT CCG ACG GGC TTA CAC CTT GGG GGC ATA AAA TAC ATG
          his leu ala pro thr gly leu his leu gly gly ile lys tyr met
             310       320       330       340
          GTC ATC CAG GGA GAG GCT GGT GCT GTC ATC CGT GGA AAG AAG GGA
          val ile gln gly glu ala gly ala val ile arg gly lys lys gly
                   360       370       380       390
          TCT GGA GGT ATT ACT ATA AAG AAG ACT GGT CAA GCT CTC GTT TTT
          ser gly gly ile thr ile lys lys thr gly gln ala leu val phe
             400       410       420       430
          GGC ATC TAT GAA GAG CCT GTG ACA CCA GGA CAG TGC AAC ATG GTT
          gly ile tyr glu glu pro val thr pro gly gln cys asn met val
                   450       460       470       480
          GTT GAG AGG TTG GGG GAT TAC CTT ATT GAC CAG GGC CTG TAG
          val glu arg leu gly asp tyr leu ile asp gln gly leu *
             490       500       510       520       530       540
GCAAAGGTCTATCATCATTTGGGGCTTAATTGTTTTTTTTTTTTTTTTTGCTCTTATTCCC
             550       560       580       590       600       610
TTTGATTTCGGTTCCAAGTGTGCATCGATCTTCATTTGAAAGCCTTAAATTGGCAGTGAA
             620       630       640       650       660       670
GTTGTTGCAGACAATAACCATGTGAGAACTAAAACATTTGTCTTGTGTTTGGTTGTTTGA
             680       690       700       710
AAAAAAAAAAAAAAAAAAAAAAAAAAAAAAAAAAAAA
```

FIG.4

```
                  10           20           30           40           50           60           70           80
Mouse         MAGWNAYIDS.LMAD..G...TCQDAAIVGYKDSPSVWAAVPGKTFVSITPAEVGVLVG..KDRSSFFVNGLTLGGQKCS
Bovine        .AGWNAYIDN.LMAD..G...TCQDAAIVGYKDSPSVWAAVPGKTFVSITPAEVGILVG..KDRSSFFVNGLTLGGQKCS
Human         MAGWNAYIDN./MAD..G...TCQDAAIVGYKDSPSVWAAVPGKTFVNITPAEVGVLVG..KDRSSFYVNGLTLGGQKCS
White birch   MS.WQTYVDEHLMCDIDGQASNSLASAIVGHDGS..VWA..QSSSFPQFKPQEITGIMKDEEPGHLAPTGLHLGGIKYM
Yeast         MS.WQAYTDN.LIGT..G...KVDKAVIYSRAG.DAVWATSGG...LSLQPNEIGEIVQGFDNPAGLQSNGLHIQGQKF.
Acanthamoeba  ..TWQSYVDTNLVGT..G....AVTQAAILGLDGNT..WASFAG...FAVTPAQGTTLAGAFNNADAIRAGGFDLAGVHYV 90          100          110          120          130          140
Mouse         VIRDSLLQDGEFTMDLRTKSTGGAPTFNVTVTMTAKTLVLLMGKEGVHGGLINKKCYEMASHLRRSQY
Bovine        VIRDSLLQDGEFTMDLRTKSTGGAPTFNITVTMTAKTLVLLMGKQGVHGGMINKKCYEMASHLRRSQY
Human         VIRDSLLQDGEFSMDLRTKSTGGAPTFNVTVTKTDKTLVLLMGKEGVHGGLINKKCYEMASHLRRSQY
White Birch   VI......Q.GEAGAVIRGKKGSGG....ITIKKTGQALVFGIYEEPVTPGQCNMVVERLGDYLID.QGL
Yeast         ....MLLRADDRSIYGRHDAEG.........VVCVRTKQTVIIAHYPPTVQAGEATKIVEQLADYLIGVQY
Acanthamoeba  T......LRADDRSIYGKKGASG........VITVKTSKSILVGVYNEKIQPGTAANVVEKLADYLIG.QGF
```

FIG. 5

```
                    10                    20
          GAAAGCAAACTTGCAGGACCGAAG 30             40             50             60
          ATG TCG TGG CAG ACG TAC GTG GAC GAG CAC CTG ATG TGC GAG ATC
          met ser trp gln thr tyr val asp glu his leu met cys glu ile
                          80             90            100            110
          GAG GGC CAC CAC CTC GCC TCG GCG GCC ATC CTC GGC CAC GAC GGC
          glu gly his his leu ala ser ala ala ile leu gly his asp gly
                         120            130            140            150
          ACC GTC TGG GCC CAG AGC GCC GAC TTC CCC CAG TTC AAG CCT GAG
          thr vla trp ala gln ser ala asp phe pro gln phe lys pro glu
                         170            180            190            200
          GAG ATC ACC GGC ATC ATG AAG GAT TTC GAC GAG CCG GGG CAC CTC
          glu ile thr gly ile met lys asp phe asp glu pro gly his leu
                         210            220            230            240
          GCC CCC ACC GGC ATG TTC GTC GCA GGT GCC AAG TAC ATG GTC ATC
          ala pro thr gly met phe val ala gly ala lys tyr met val ile
                         260            270            280            290
          CAG GGT GAA CCC GGT CGC GTC ATC CGT GGC AAG AAG GGA GCA GGA
          gln gly glu pro gly arg val ile arg gly lys lys gly ala gly
                         300            310            320            330
          GGC ATC ACC ATA AAG AAG ACC GGG CAG GCG CTG GTC GTC GGC ATC
          gly ile thr ile lys lys thr gly gln ala leu val val gly ile
                         350            360            370            380
          TAT GAC GAG CCC ATG ACC CCT GGG CAG TGC AAC ATG GTG GTG GAG
          tyr asp glu pro met thr pro gly gln cys asn met val val glu
                         390            400            410            420
          AGG CTT GGC GAC TAC CTC GTT GAA CAA GGC ATG TAG
          arg leu gly asp tyr leu val glu gln gly met  *

430       440       450       460       470       480
          ACTGGCTGATCCATGGCTTCCACGTCTCCACGATCGATGATGATCATACAGTTTTTCACG
              490       500       510       520       530       540
          TTCTTTTAAACATCTATTGGAATATATATGGGGCTTCTCCTCTTTTACCGGCTCTGGTCA
              550       560       570       580       590       600
          TGGATCACTGATGACCAGTTGCTCTGGAAGTTTCATTTGTAATGCCATCTTGGCTTTCTA
              610       620       630       640
          TCTTCTTCAATGTTTTTTTTTTCTTTTCGGTTAAAAAAAAA
```

FIG.16

METHOD OF PRODUCTION OF BIRCH POLLEN ALLERGEN P14

This application is a divisional of application Ser. No. 07/846,992, filed Jun. 6,1992, now pending, which is a continuation in part of application Ser. No. 07/683,832, filed Apr. 11, 1991, now abandoned.

1. FIELD OF THE INVENTION

The invention provides recombinant DNA molecules which code for polypeptides, and the polypeptides per se, that have at least one epitope of a P14 pollen allergen of a tree of the order Fagales, particularly birch (*Betula verrucosa*), or the entire P14 allergen protein, and exhibit the same or similar antigenicity as a P14 allergen. The invention also provides replicable microbial expression vehicles and microorganisms for use in processes for producing such allergenic polypeptides. Methods are provided for purification of P14 allergen as well as for the diagnosis and therapy of allergic diseases using the synthetic polypeptides of the invention.

2. BACKGROUND OF THE INVENTION

In the springtime large parts of the populations of Central, Eastern and Northern Europe, America and Australia suffer from allergic symptoms (rhinitis, conjunctivitis, dermatitis and pollen asthma). Proteins which can be isolated from pollen of trees of the order Fagales, in particular from pollen of birch, alder, hazel, hornbeam and oak, are responsible for most of these allergic symptoms (1).

At least 10% of the population suffers from pollen allergies at various times and to varying extent. These allergies are mediated ,by IgE antibodies which react with pollen proteins. The possibility exists for a therapy for pollen allergies by hyposensitization, i.e., by the regular and slowly increasing administration of the proteins producing the allergy.

Diagnostic methods for allergic diseases, such as RIA (radioimmunoassay), IRMA (immuno-radiometric assay), RAST (radio-allergosorbent test), ELISA (enzyme-linked immunosorbent assay), magnetic allergoabsorbent test, immunoblots, LIA (luminescence immunosay), Histamine release assays and others depend greatly upon the availability of pure allergens. Protein extracts from pollen isolated from natural sources are difficult to standardize because preparations vary from batch to batch. For example, they may contain unwanted constituents, and/or certain proteins may be lost in the extraction procedure and be missing from the final separation (2). Clearly, diagnostic tests which employ well defined allergens that can be reproducibly prepared would be superior to tests which employ raw pollen extracts with an insufficiently defined mixture of allergens and other components. Recombinant DNA production of allergenic polypeptides, or allergenic fragments thereof, would allow more reproducible preparations of allergens of defined content for standardized diagnostic and therapeutic methods.

Allergens may be purified to homogenity from pollen by known protein/chemical methods, for example, by means of affinity chromatography (3). These methods are relatively costly and require pollen as an ill-defined source which cannot be standardized. It would, therefore, be cheaper and more efficient to use recombinant DNA methods to produce an allergenic protein, or fragments of that protein.

Hyposensitization has proved to be an effective therapy in allergic diseases. This therapy consists of parenteral or oral administration of allergens in increasing doses over a fairly long period of time. Like diagnostic methods, it requires pure and well defined allergens. The use of purified recombinant allergens or synthetic peptides would greatly reduce the risk of sensitizing patients to unwanted components.

3. SUMMARY OF THE INVENTION

Figure 1B:
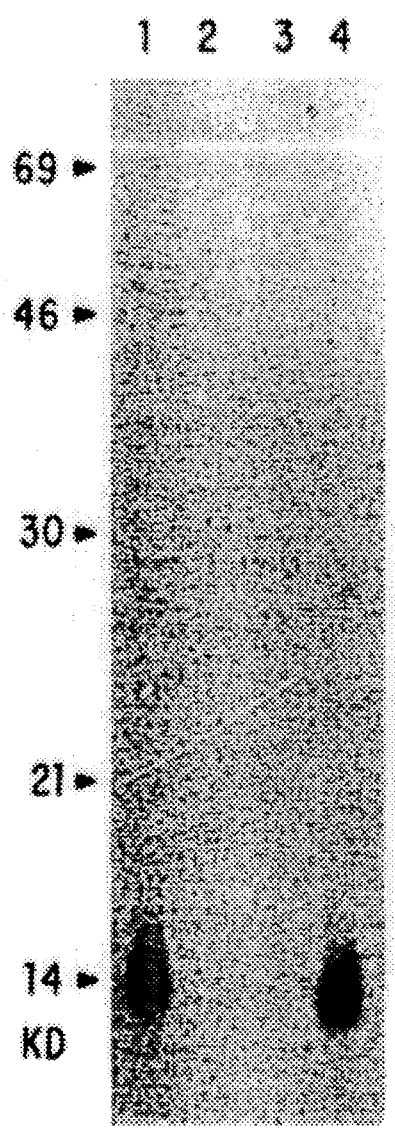

This invention concerns pollen allergens, for example, of white birch (*Betula verrucosa*), called P14. These pollen allergens are immunologically closely related to allergens which occur in pollen of far distantly related plant species, particularly in trees of the Fagales order (birch, alder, hazel, hornbeam and oak), in grasses and weeds. The cross-reactivity of IgE antibodies of patients to these pollen allergens is illustrated in FIGS. 1A and 1B.

The present invention provides recombinant DNA molecules which contain a nucleotide sequence that codes for a polypeptide which exhibits the same or similar antigenic properties as a natural allergen, P14, which occurs in trees of the order Fagales and other pollen producing plants, or a polypepride which comprises at least one epitope of such allergens. The invention provides the complete cDNA sequence of a P14 allergen and hence the complete deduced amino acid sequence. Additionally, the invention includes (a) nucleotide sequences which hybridize with such a cDNA sequence under high stringency and encode a polypeptide having at least one epitope of a P14 allergen and (b) nucleotide sequences which can be derived from such allergenic polypeptides by degeneracy of the genetic code. This nucleotide sequence can be expressed as a P14 allergen, or as a polypeptide which comprises at least one epitope thereof. In a preferred embodiment, this cDNA sequence contains the whole sequence or parts of the sequence set forth in the Sequence Listing as SEQ ID NO:2.

As concerns their IgE binding, pollens of birch, alder, hazel, hornbeam, oak, grasses and weeds possess similar allergens as the P14 allergen. The present invention therefore relates not only to a P14 allergen of birch, but as well to P14 pollen allergens of other species which are coded by DNA sequences that are able to hybridize with the nucleotide sequence of a birch P14 allergen under stringent conditions or can be derived from such polypeptide by degeneracy of the genetic code. Hybridization of a polynucleotide with another polynucleotide under stringent conditions requires at least a 60% identity between such polynucleotides at the nucleic acid level.

Such stringent conditions entail washing of hybridized nitrocellulose filters as follows:

a) For DNA/DNA and DNA/RNA hybridizations: A temperature of 55° C., a salt concentration of 150 mM NaCl and 15 mM $Na_3citrate \times 2$ $H_2O$, at pH 7,0, and SDS (Sodium Docedyl Sulfate) detergent at a concentration of 0,1% (w/v).

(b) For oligodeoxynucleotides/DNA hybridizations: A temperature of 55° C., a salt concentration of 1M NaCl and 10 mM $Na_3citrate \times 2$ $H_2O$, at pH 7,0, and SDS (Sodium Dodecyl Sulfate) detergent at a concentration of 0,5% (w/v). In this context "oligodeoxynucleotide" refers to an oligomer of a single stranded DNA of up to 100 nucleotides in length.

In addition, this invention provides expression plasmids that contain a nucleotide sequence as described above and hose cells which harbor these expression plasmids.

This invention also provides compositions containing synthetic polypeptides which exhibit the antigenicity of parts or of the whole of a birch P14 allergen or of allergens of other plants which, because of a high degree (at least 50%) of amino acid homology, exhibit antigenic cross-reactivity to parts or to all of a birch P14 allergen, i.e., antibodies or cellular antigen binding sites which are actually directed to birch P14 allergen are likewise able to bind to these molecules. These synthetic polypeptides include fusion and nonfusion polypeptides which contain a polypeptide portion that possesses the antigenicity of a part or of all of a P14.

It may be concluded from the results of IgE immunoblots, cross-inhibition tests, clinical tests and Northern (RNA) blots (4–9) (FIGS. 1A, 1B and 3) that homologous IgE-binding polypeptides exist in the pollen of closely related trees of the order Fagales and for distantly related pollen producing plants. For this reason this invention provides polypeptides which exhibit the same or similar antigenicity as the related P14 pollen allergens of birch, alder, hazel, hornbeam, oak, grasses and weeds.

Figure 12:
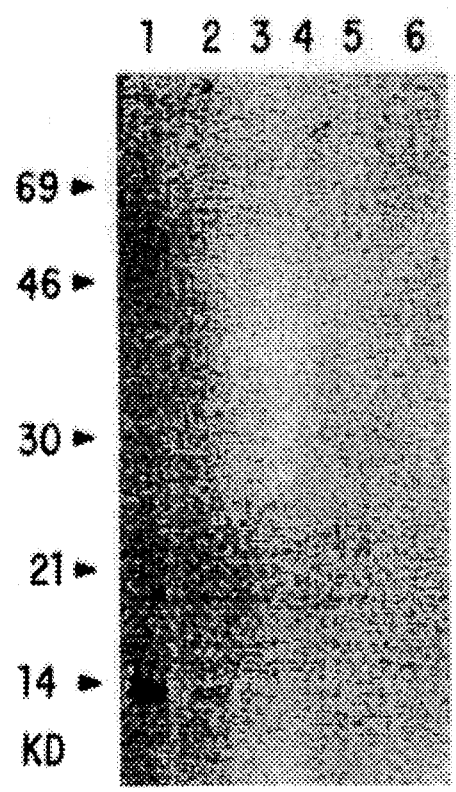

A computer search in the available sequence data banks (EMBL, MIPSX, Swissprot) for proteins whose sequences share homology with birch P14 revealed a significant homology between P14 and a cytoskeletal protein (profilin) which is present in a variety of eukaryotes (10–14) (FIG. 5). This homology raises the possibility of the cross-reactivity of IgE antibodies of patients with human profilin. This autoreactivity has been demonstrated (FIG. 12).

In this way, a molecular system is provided which permits testing the hypothesis: whether autoimmune mechanisms play a role in allergic and atopic diseases. Initial data show that patients whose IgE antibodies react with P14 represent a group that suffers from allergic symptoms during a large part of the year and who do not respond satisfactorily to immunotherapy or conventional therapy. It follows from this that P14, or recombinant or chemically synthesized IgE-binding polypeptides with sequences that match the sequence deduced from P14 cDNA, can be used to characterize a certain group of multivalent allergics as well as a prognostic markers for hyposensitization therapy.

In addition, this invention presents an efficient method for the production and purification of pollen protein as well as of recombinant or synthetic P14 polypeptide or allergenic fragments thereof. The purification method is based on the affinity of profilin polypeptides for poly(L-proline) (15, 16), and the present inventors' showing of homology between profilins and P14 allergens. Since the binding of pollen protein and of recombinant P14 to poly(L-proline) has been shown herein (FIGS. 8, 9 and 10), a method is thereby provided for immobilizing (and affinity separation of) this allergen. Thus, certain diagnostic tests can be set up (for example, poly(L-proline) may be used instead of an antibody for binding profilin in ELISAs). Likewise, forms of therapy are possible which by means of poly(L-proline) bind P14 and analogous polypeptide allergens. Since there are indications that patients who suffer from autoimmune diseases form antibodies against P14, this polypeptide or homologous polypeptides could be used for diagnosis or therapy of these diseases.

4. BRIEF DESCRIPTION OF THE FIGURES

The following figures and description aid in understanding the field and scope of the invention.

FIG. 1A: IgE immunoblot: Pollen proteins from birch (B), hornbeam (CA), alder (A) and hazel (C) were separated by means of a 12.5% polyacrylamide electrophoresis and blotted on nitrocellulose. The nitrocellulose was cut into strips (1–5) which were incubated with dilutions of a serum (1:5, 1:10, 1:20, 1:40, 1:80, respectively) of a selected patient whose IgE antibodies recognized most important birch pollen allergens. Arrows and stars indicate molecular weights. Bound serum IgE was detected by means of an autoradiograph of $^{125}$I-labeled antihuman IgE antibodies of rabbit bound thereto. The IgE-binding proteins of birch, alder, hazel and hornbeam matched one another, which demonstrates the similarity of the antigens.

FIG. 1B: IgE immunoblot inhibition: mugwort profilin that had been purified by poly(L-proline) affinity chromatography had been blotted on nitrocellulose after polyacrylamide gel electrophoresis. The 1:10 dilution of the serum from a patient allergic to birch profilin was pre-incubated in lane 1 with control proteins from *E. coli*, in lane 2 with recombinant birch profilin, in lane 3 with purified profilin from *Phleum pratense* (grass) and in lane 4 with buffer (negative control) and used for detection of mugwort profilin. Binding of patients' IgE to mugwort profilin can be blocked with recombinant birch profilin and purified grass profilin demonstrating common IgE binding properties of these related proteins. In the control lanes 1 and 4 binding of patients' IgE to mugwort profilin occurs.

Figure 2:
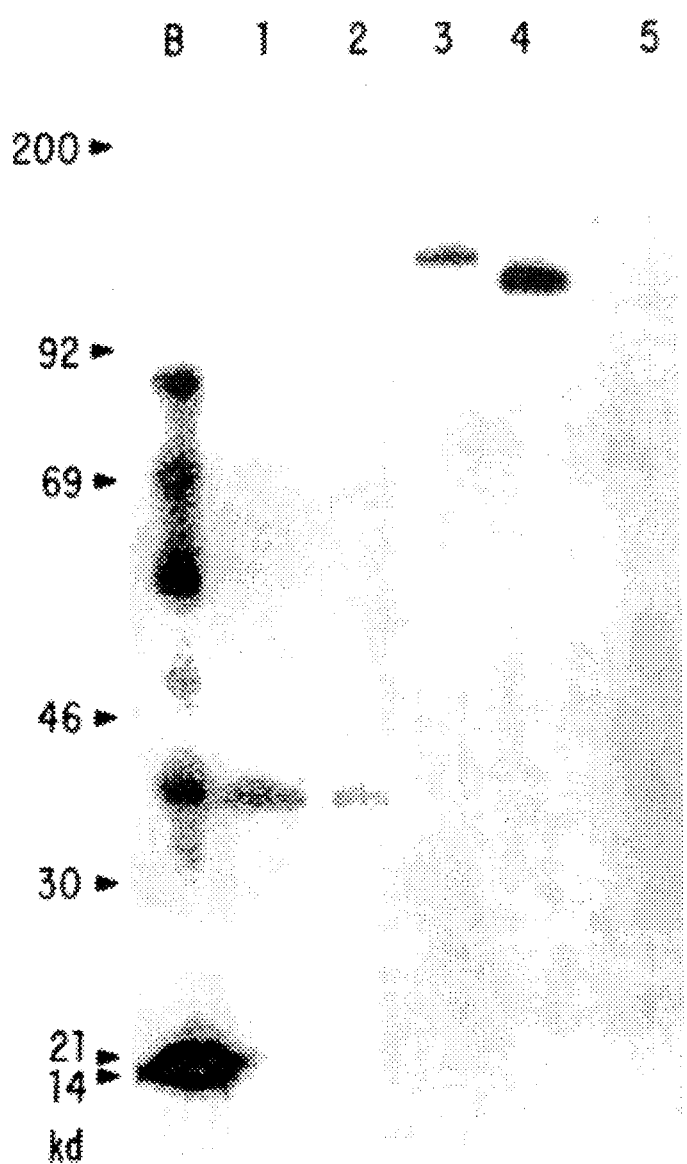

FIG. 2: IgE immunoblot: Proteins were separated by means of a 7.5% polyacrylamide gel electrophoresis and blotted on nitrocellulose. Lane B: birch pollen proteins; lane 1: proteins from *E. coli* Y1089 (lysogenic host); lane 2: proteins of *E. coli* Y1089 inoculated with the lambda gt11 phage without insert; lane 3: proteins from *E. coli* Y1089 inoculated with a recombinant phage containing a birch pollen derived cDNA encoding an IgE binding polypeptide (positive control); lane 4: proteins from *E. coli* Y1089 inoculated with recombinant phages which contain the 3'-portion of P14 cDNA which codes for an IgE-binding epitope (as underlined in FIG. 4); lane 5: proteins from yeast (*Saccharomyces cerevisiae*). Recombinant 6-galactosidase fusion proteins with IgE-binding capacity whose molecular weights were between 115 and 130 kD (lanes 3 and 4) were detected with $^{125}$I-labeled antihuman IgE antiserum from rabbit. No comparable IgE binding takes place in lanes 1, 2 and 5, while lane B shows the patient's IgE-binding profile with birch pollen proteins.

Figure 3:
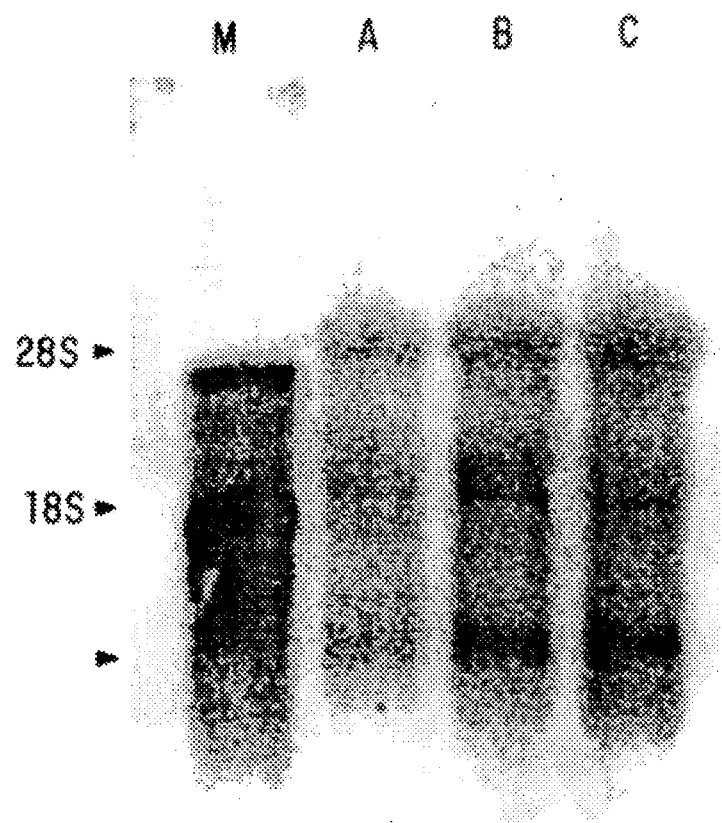

FIG. 3: Northern (RNA) blot: Ten μg pollen RNA of alder (lane A), birch (lane B) and hazel (lane C) and as a marker RNA of *E. coli* (lane M) were blotted on nitrocellulose. The part of the P14 cDNA underlined in FIG. 4 hybridizes with pollen mRNA of alder, birch and hazel and under stringent conditions (0.75×SSC, 0.1% SDS, 50° C.) produces a signal at 800 bases (indicated by an arrow). The position of ribosomal bands is indicated by "28S" and "18S".

FIG. 4: cDNA sequence of birch P14. The coding region begins with ATG (nucleotides 80–82) and ends with the stop codon TAG (nucleotides 479–481). The deduced amino acid sequence is illustrated under the DNA sequence. The P14 sequence, which within a fusion protein is able to bind IgE of patients and therefore represents at least one epitope, is shown underscored (see Section 5.4).

FIG. 5: Comparison of the derived amino acid sequence of birch P14 with the amino acid sequences of profilins of human (13), calf (14), mouse (12), yeast and Acanthamoeba (10). Identical amino acid residues ate marked. The percentage of identical amino acid residues between P14 protein of birch and homologs amounts to for human protein, 28% for homologous proteins of calf and mouse, 26% for yeast protein and 25% for Acanthamoeba protein.

Figure 6:
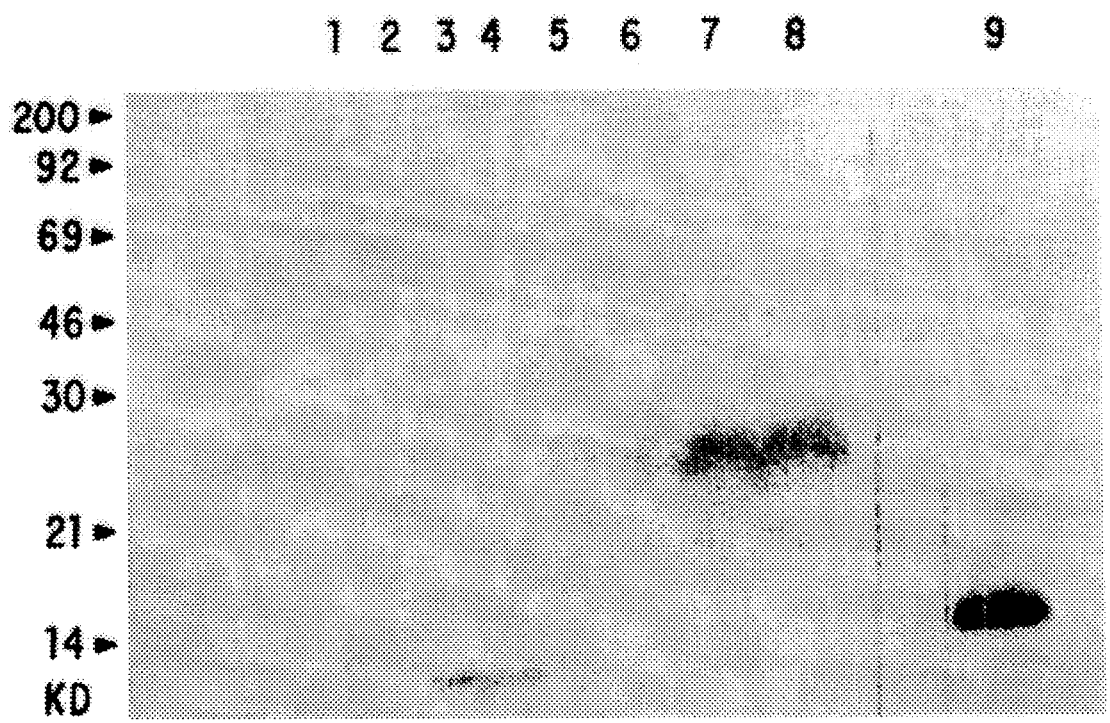

FIG. 6: Western (protein) blot of a polyacrylamide gel probed with IgE antibodies of patients with tree pollen allergy. Lane 1: proteins of *E. coli* JM105 without any plasmid; lane 2: proteins of *E. coli* JM105 with the plasmid pKK223-3 without an insert lanes 3 and 4: proteins of *E. coli* JM105 with that plasmid derived from pKK223-3 which expresses the P14 protein of the inserted cDNA as nonfusion protein; lane 5: *E. coli* AR58 proteins; lane 6: *E. coli* AR58 with the plasmid pEXB without an insert; lanes 7 and 8: extracts from *E. coli* AR58 transformed with the plasmid derived from pEXB which expresses P14 cDNA as fusion protein; lane 9: birch pollen protein extract (positive control).

Figure 7:
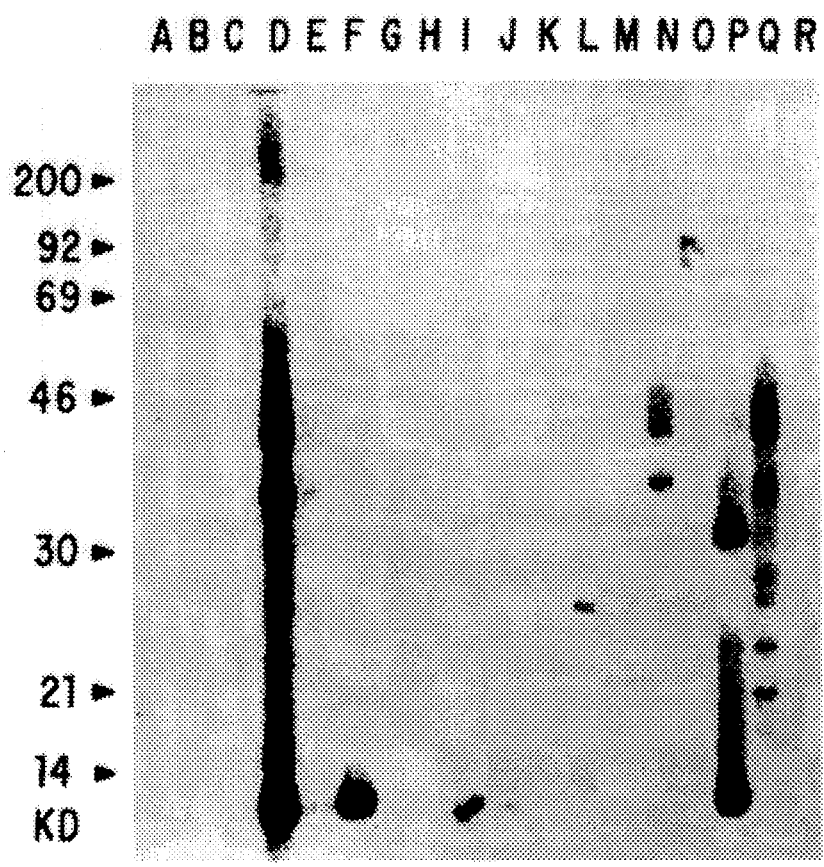

FIG. 7: Sara from various allergic patients were tested for their IgE reactivity with respect to recombinant P14 which was expressed in pKK223-3. Patients (lanes) D, E, F, I, J, and P show IgE binding to the recombinant P14. Lane R is a serum pool from non-allergic individuals. The recombinant P14 was not purified and, therefore, reactivity of patients' IgE with proteins from *E. coli* was seen.

Figure 8:
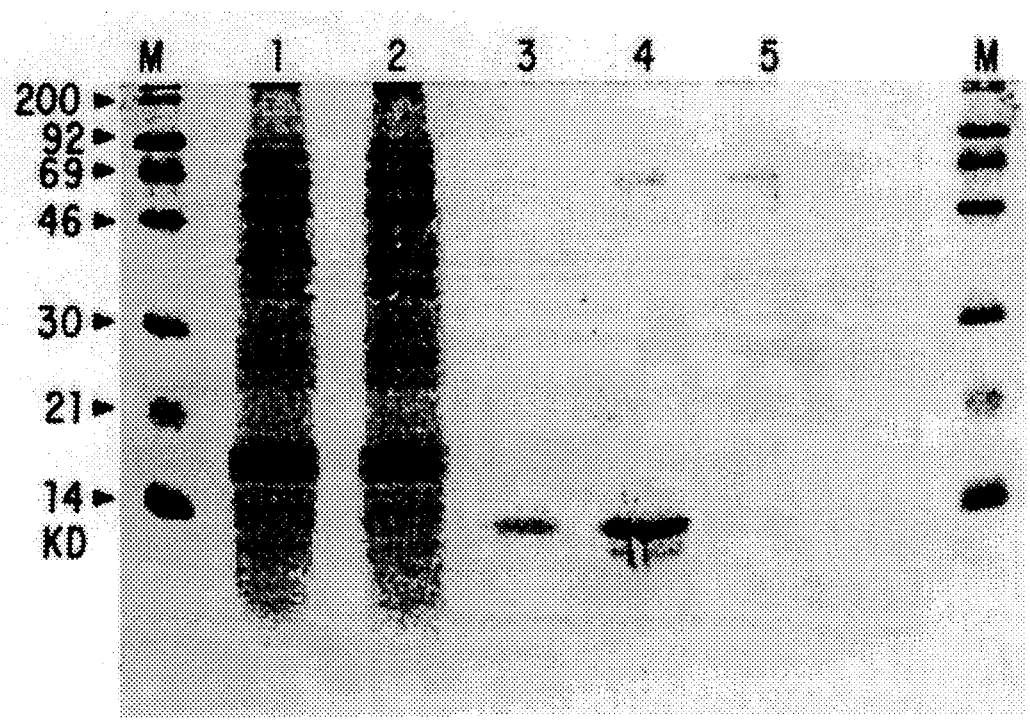

FIG. 8: Coomassie stained polyacrylamide gel. Lane M: molecular weight marker; lane 1: total pollen proteins of birch; lane 2: birch pollen proteins from which P14 was removed by the affinity method (flow through); lanes 3, 4 and 5: eluted P14. Proteins were applied to the gel and stained to indicate migration. As can be seen from lanes 3, 4 and 5, P14 can be purified by affinity chromatography to poly(L-proline) sepharose.

Figure 9:
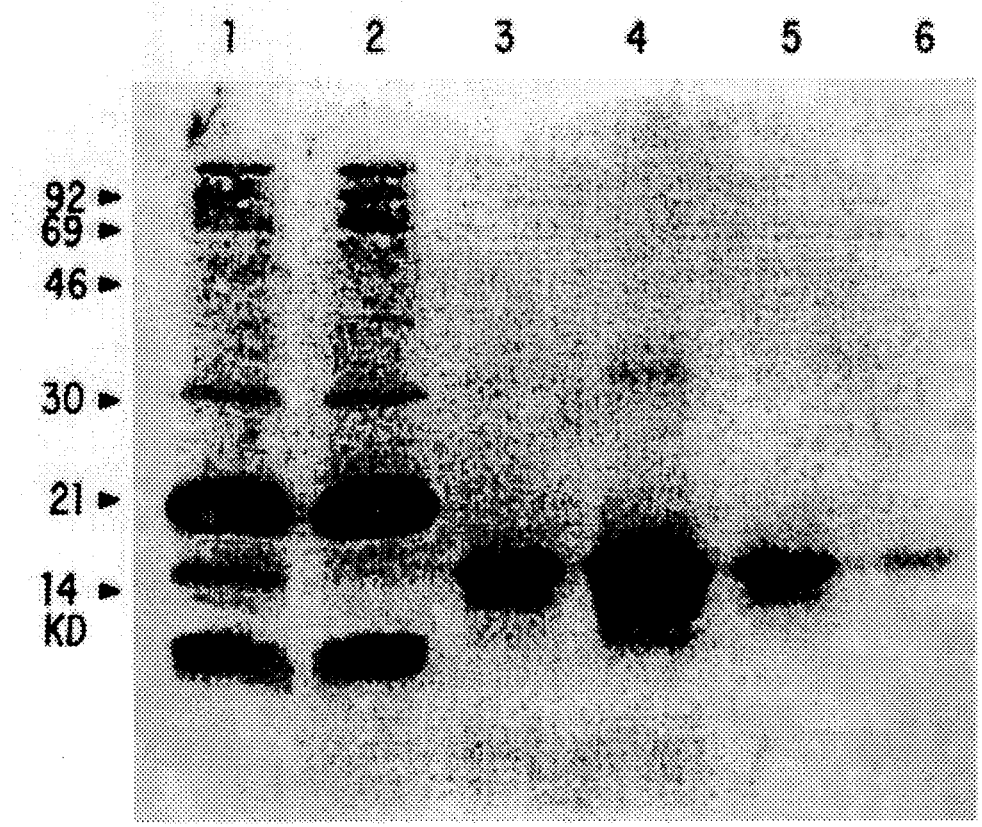

FIG. 9: IgE immunoblot: A probe of proteins obtained in the same way as in FIG. 8 was transferred to nitrocellulose and incubated with serum IgE of a patient who recognizes most birch pollen allergens. Lanes 1–5 contain the same material as in FIG. 8; lane 6 contains the molecular weight marker. This immunoblot shows that birch profilin can be purified to apparent homogeneity from other allergens.

Figure 10:
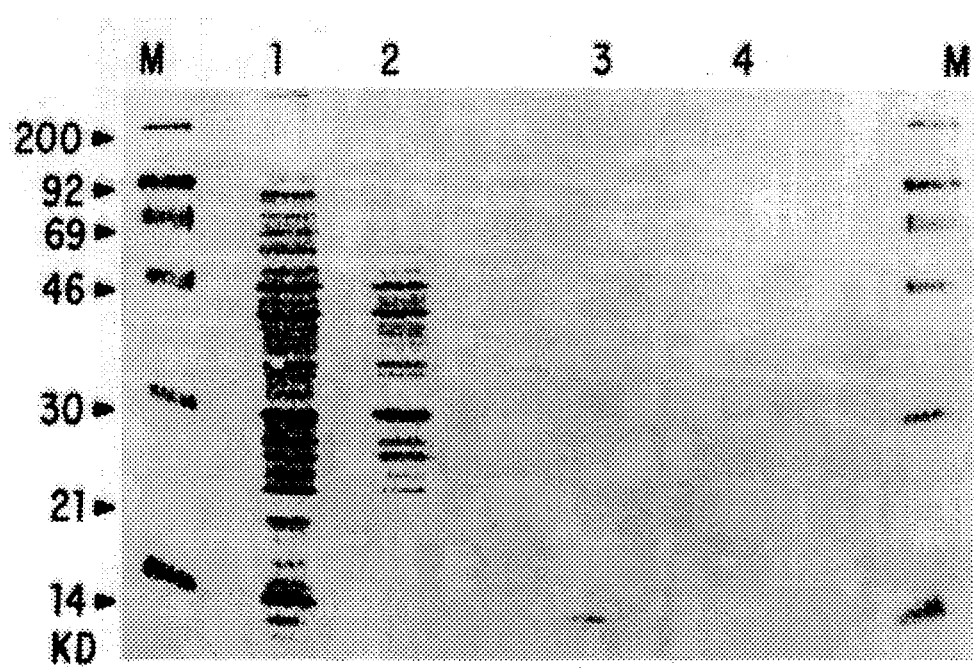

FIG. 10: Coomassie-stained polyacrylamide gel. Lane M: molecular weight marker; lane 1: total proteins of *E. coli* JM105 with the plasmid derived from pKK223-3 that expressed the P14 cDNA; lane 2: protein fraction after removal of the recombinant P14 by affinity chromatography to poly(L-proline) sepharose; lanes 3 and 4: purified recombinant P14-eluted fractions.

Figure 11:
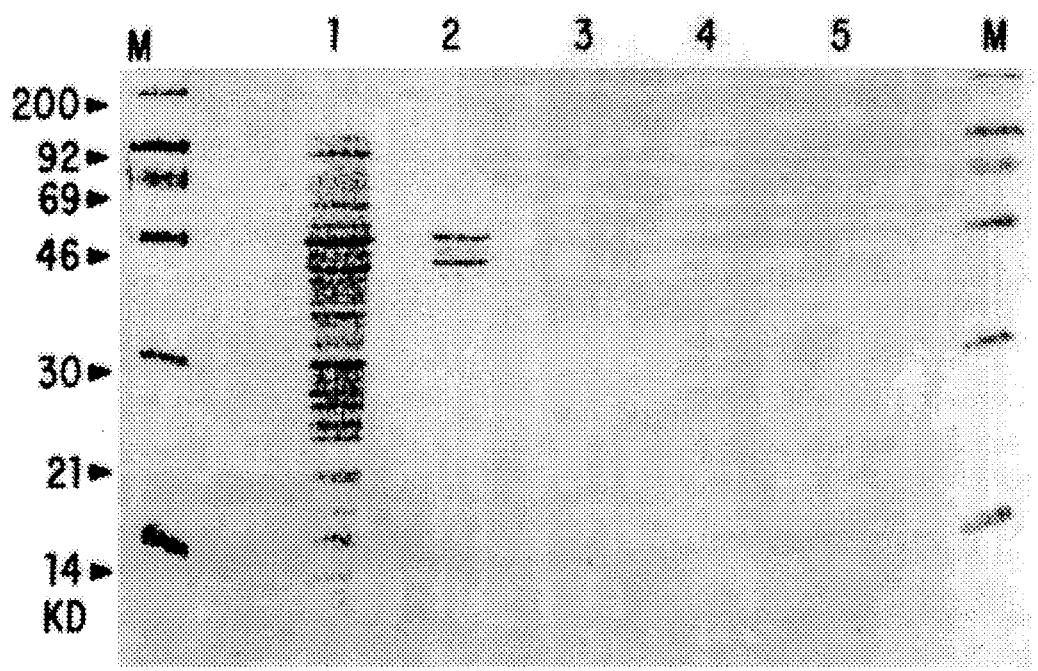

FIG. 11: Coomassie-stained polyacrylamide gel. Lane M: molecular weight marker; lane 1: total protein from *E. coli* jM105 with the plasmid pKK223-3 without insert; lane 2: protein fraction after poly(L-proline) purification; lanes 3, 4 and 5: eluted fractions. These results show that no protein with similar properties to P14 can be isolated from the expression system without insert.

FIG. 12: IgE immunoblot: Purified human profilin was loaded on a 12% polyacrylamide gel and blotted on nitrocellulose. Strips of the nitrocellulose were cut and incubated as follows: Strip 1 was incubated with serum IgE of a patient who recognized besides P14 and the major birch pollen allergen, Bet v I, allergens in the molecular range between 30 and 90 kD. Strip 2 was incubated with serum IgE from a patient who recognized only P14 in birch pollen extracts; strip 3 was incubated with serum from a patient whose serum IgE was directed only against Bet v I; strip 4 was incubated with the serum from a patient allergic to mites; strip 5 with serum from a group of nonallergic donors and strip 6 shows the buffer control. IgE binding was detected with a $^{125}$I-labeled antihuman IgE antiserum of rabbit. Cross-reactivity was shown for strips 1 and 2. This data demonstrates that serum IgE that reacts with birch pollen also cross-reacts with human profilin.

Figure 13:
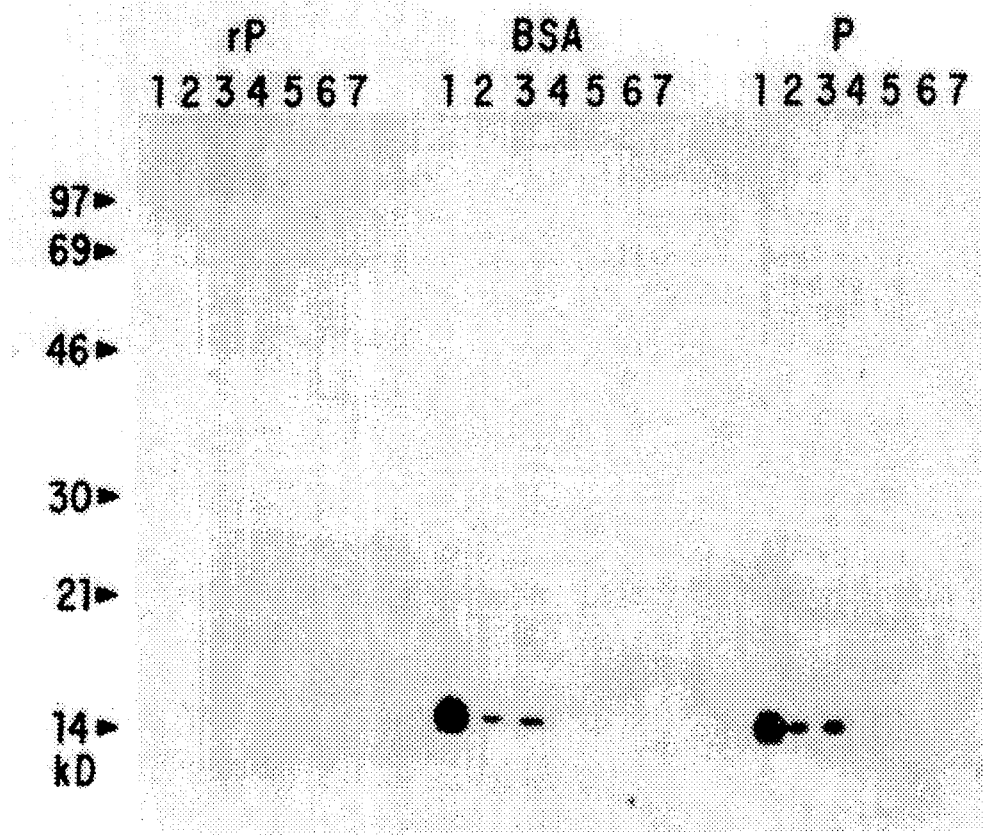

FIG. 13: IgE-inhibition: Purified celery profilin was subjected to SDS-Page, blotted to nitrocellulose (1 µg/cm). Nitrocellulose strips where incubated with 1:10 dilutions of sera from birch pollen profilin allergic patients (lanes 1–3), from patients allergic to the major birch pollen allergen Bet v I but not to profilin, a serum pool of no allergic individuals (lane 4) and with buffer without addition of serum (lane 5). The serum dilutions where preincubated with 5 µg of purified recombinant birch profilin each (rP), 5 µg of BSA (BSA), and with serum dilution buffer(P). Binding of IgE of the patients 1–3 to celery profilin can be blocked with purified recombinant birch profilin indicating common IgE epitopes of birch and celery profilin.

Figures 14A, 14B:
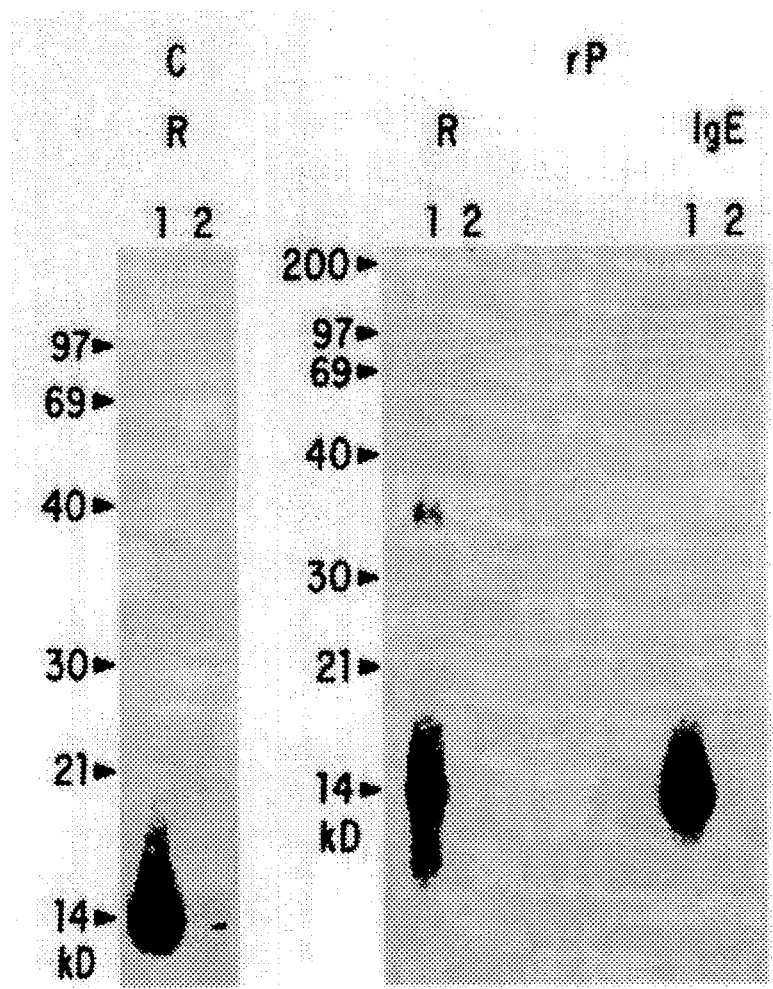

FIG. 14: Immunoblots: Purified celery profilin (C) and recombinant birch profilin (rP) is recognized by the rabbit anti celery profilin antibody (R: lane 1). Recombinant birch profilin also binds patients IgE (IgE: lane 1). No binding is seen in lane 2 (buffer control without addition of antibody or serum).

Figures 15A, 15B:
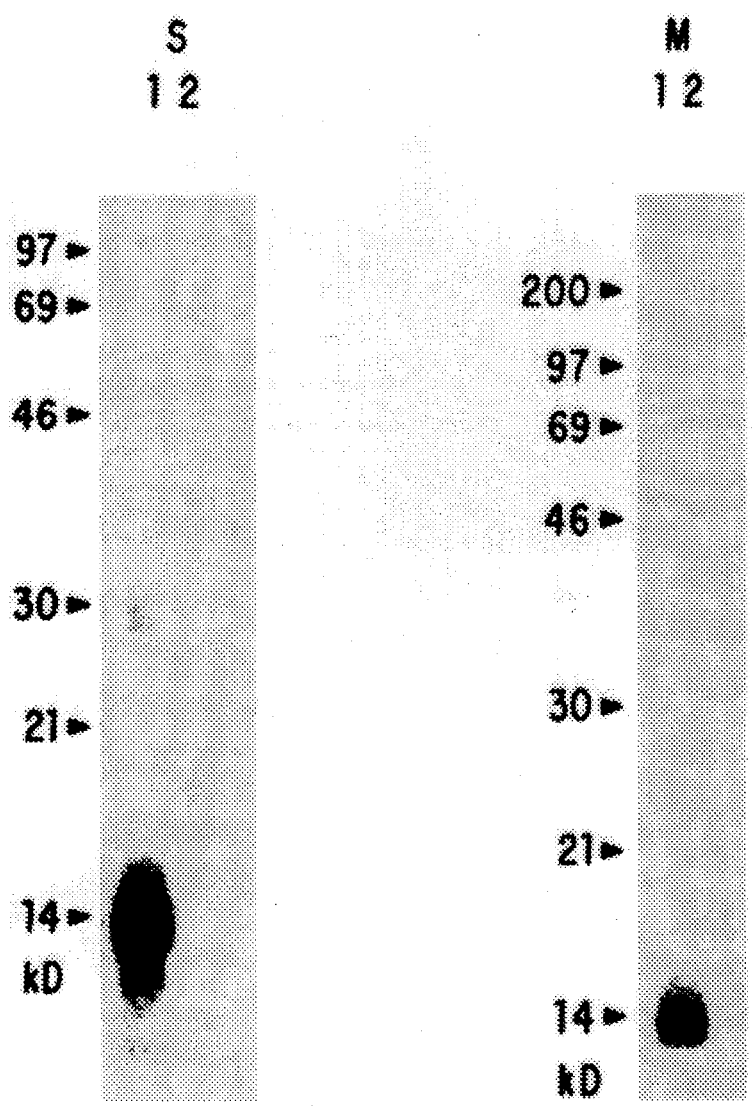

FIG. 15: Immunoblots: Purified profilin from rye (*Secale cereale* S) and from mugwort (*Artemisia vulgaris* M) binds the rabbit anti celery profilin antibody (lanes 1) whereas in the buffer control (lane 2) no binding was found.

Bound rabbit antibody in FIGS. 14 and 15 was detected with $^{125}$J donkey anti rabbit antibody from Amerham, UK. Bound serum IgE in FIGS. 13 and 14 was detected with $^{125}$J rabbit anti human IgE from Pharmacia, Sweden.

FIG. 16: cDNA and deduced amino acid sequence of profilin from pollen of timothy grass (*Phleum pratense*)

Figure 17:
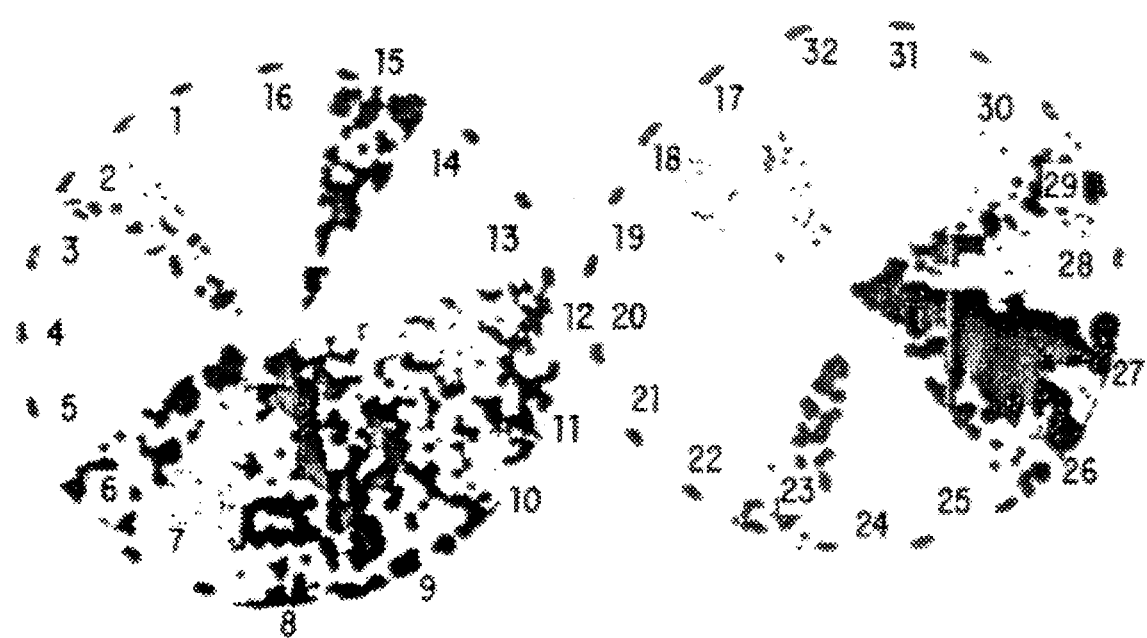

FIG. 17: IgE-binding of patients IgE to plaquelifts of lambda gt 11 phages containing the cDNA insert encoding timothy grass profilin 30 grass pollen allergic patients were tested for IgE binding to lambda gt 11 phages that express profilin from timothy grass which was bound to nitrocellulose sectors. Sector 31 shows a serum pool from non allergic individuals and sector 32 the buffer control without addition of serum. Serum IgE of patients 2, 6, 7, 8, 9,10,11,12,15, 17,18,21,23,26,27,28,29 and 30 bound to the recombinant timothygrass profilin expressed in lambda gt 11. All these patients also displayed IgE reactivity to birch profilin. Patients 1, 3, 4,5,13,14,16,19,20,22,24, and 25 who were allergic to other grass pollen allergens did not show any IgE reactivity to timothy grass profilin. Bound serum IgE was detected as described in FIG. 13.

5. EXAMPLES

The invention can be understood by reference to the following examples:

5.1. Construction of the cDNA gene bank

Pollen (Allergon AB Engelholm, Sweden) which was examined for purity by means of light and electron microscopy, was used for the isolation of polyadenylated RNA (17, 18). cDNA synthesis was carried out with oligo-dT and random primers (19, 20), the ends of the cDNA were cleanly digested with T4-polymerase and provided with EcoRI-linkers. The cDNA with linkers was ligated and packed in dephosphorylated lambda gt11 arms (21). A cDNA gene bank of 800,000 independent clones was produced.

5.2. Screening of the cDNA gene bank

IgE screening of the birch pollen cDNA gene bank was performed as described (22). IgE-binding clones were enriched and phage DNA was prepared therefrom (23). The inserts were cut out with EcoRI and the fragments were subcloned in the plasmid pUC18 (24). The DNA sequence of a clone was obtained (25). Although it was complete at the 3'-terminus (poly-A tail), it lacked a part of the 5'-terminus including the start codon as well. This partial sequence is underscored in FIG. 4. Therefore the original gens bank was again screened with oligodeoxynucleotides which were complementary to the coding region (26) and two independent clones were obtained.

5.3. RNA (Northern) blots

Ten μg of total RNA from pollen of alder, birch and hazel were separated by means of a denaturing gel electrophoresis and blotted on nitrocellulose (27, 28). A P14 cDNA probe, as underlined in FIG. 4, was $^{32}$P-labeled by means of random priming (29). Prehybridization and hybridization were carried out by standard methods (23). The blots were washed with 0.75×SSC (20×SSC=3M NaCl, 0.3M Na citrate, pH 7.0), 0.1% SDS (sodium dodecyl sulfate) at 50° C. and autoradiographed (Hyperfilm MP, Amersham, London, UK).

5.4. Expression of Birch P14 cDNA 5.4.1 Expression of the 3'-terminus of the cDNA in lambda gt11 phages (FIG. 2)

An incomplete cDNA clone which codes for a part of P14 was obtained by means of IgE screening (22) as described in Section 5.2. The lysogenic E. coli strain Y1089 was inoculated with recombinant lambda gt11 phages, containing an insert as underlined in FIG. 4, and the 6-galactosidase fusion protein was recovered from the mixture (19). The construction would predict that a fusion protein having a molecular weight of 116 kD would be produced. The mixture was subjected to electrophoresis on a 7.5% polyacrylamide gel and was blotted on nitrocellulose. The fusion protein was detected by means of IgE antibodies in patient serum and an iodine-labeled rabbit antihuman IgE antibody (Pharmacia, Uppsala, Sweden) (FIG. 2). As shown in FIG. 2, a fusion protein having a molecular weight of between 115 kD and capable of binding to IgE antibodies was observed.

5.4.2. Expression of complete P14 cDNA as fusion and nonfusion protein

The complete cDNA that codes for P14 contains a prokaryotic ribosome binding site (Shine-Dalgarno sequence (30)) and was inserted into the EcoRI sites of plasmids pKK223-3 (31) or pEXB (32) to obtain P14 as a nonfusion protein or a fusion protein of P14 with the lambda cII protein. IgE-binding clones were obtained by means of serum IgE and a colony screening method (33) and were examined by means of DNA restriction analysis. Recombinant proteins were tested for their binding capacity with respect to patient IgE antibodies as described (22) (FIG. 6).

5.5. Purification of birch pollen P14 and recombinant P14

P14 from birch pollen and recombinant P14 were purified by means of an affinity method by a batch process (cf. 15, 16) which is suitable-for the profilins of Acanthamoeba (10), yeast (11) and man (13). Birch pollen and E. coli cells, which contain the plasmid that codes for P14, were lysed in PHEM-TX buffer (2×PHEM-TX: 120 mM PIPES (piperazine-1,4-bis(2-ethanesulfonic acid)), 50 mM HEPES (N-2-hydroxyethylptperazine-N'-2-ethanesulfonic acid), 20 mM EGTA (ethylene glycol-bis(6-aminoethyl ether)-N,N, N',N'-tetraacetic acid), 4 mM MgCl$_2$, 10 mM glucose, 20 μg/ml leupeptin, 156 μg/ml benzamidin, 80 μg/ml aprotinin, 1 mM PMSF (phenylmethyl sulfonyl fluoride), 1.5% Triton-X100, pH 7.2) and the lysate was centrifuged for one hour at 65000×g at 4° C. The supernatant was inoubated overnight at 4° C. with poly(L-proline) coupled to BrCN-activated Sepharose 4B (Pharmacia, Uppsala, Sweden). Then the affinity matrix was washed three times with a double volume each time of TBS-ATP (20 mM TRIS, 150 mM NaCl, 0.5 mM ATP (adenosine triphosphate), pH 7.6) and then eluted for five minutes at room temperature with a double volume of elution buffer I (TBS-ATP with 2M urea). The supernatant was collected. The procedure was repeated twice with elution buffer II (TBS-ATP with 6M urea) and the supernatants were dialyzed against distilled water at 4° C. The dialysates, which contained the proteins, were lyophilized and analyzed by means of polyacrylamide gel electrophoresis and IgE immunoblot (FIGS. 8, 9, 10 and 11).

5.6. IgE-binding capacity of a protein expressed from a fragment of P14 cDNA which contains an IgE-binding epitope The 3'-region of P14 cDNA (bp 419–478) was cloned in the EcoRI site of lambda gt11 and expressed as an IgE-binding polypeptide (21) as shown in FIG. 2. The 6-galactosidase fusion protein (lane 4) bound strongly to IgE of the patient, while the control lanes 1 and 2 exhibited no IgE binding for the proteins of E. coli Y1089 and the proteins of E. coli Y1089 which were inoculated with lambda gt11 phages without an insert. This example shows that a partial cDNA clone which codes for a protein having at least one epitope of the P14 molecule was obtained. It follows from this that partial cDNA clones which code for such incomplete P14 polypeptides may be useful for a therapy or diagnosis in a way similar to the complete P14 molecule or homologous proteins.

5.7. Demonstration of polynucleotides and polypeptides homologous to P14 within the order Fagales The Northern (RNA) blot (FIG. 3) shows that the P14 cDNA sequence (polynuoleotide underlined in FIG. 4) is able to cross-hybridize with pollen mRNA from alder and hazel under stringent conditions (requirements of stringency are defined in 3. Summary of the Invention). Therefore, the sequence homology of the corresponding allergens of trees of the order Fagales can already be demonstrated at the nucleic acid level. FIG. 1A already showed a similar IgE-binding capacity of proteins of alder, hazel and hornbeam homologous to P14. It follows from this that P14 cDNA codes for polypeptides of similar IgE-binding capacity and antigenicity to closely related tree pollen allergens.

5.8. Sequence analysis

FIG. 4 shows the sequence of the cDNA that codes for birch P14, and the deduced amino acid sequence of the coding region. It contains the complete protein coding region. The sequence of the peptide that, coupled to 6-galactosidase, represents an IgE-binding epitope is underlined in the figure (see Example 5.4).

FIG. 5 illustrates the sequence homology between the P14 protein of birch and of human, mouse, calf, yeast and Acanthamoeba profilins (13, 12, 14, 11, 10).

The cross-reactivity of patient IgE with birch P14 and human profilin is shown in FIG. 12. Similar chemical properties of these related proteins were likewise shown by their common affinity to poly(L-proline) (FIGS. 8 and 10). These data indicate that the profilins of species which are as far apart in evolutionary terms as humans and birch are able to act as cross-reactive parallergens that may lead to an IgE autoimmune reactivity in patients.

5.9. Expression of P14 coding cDNA in E. Coli as fusion or nonfusion protein and detection of IgE-binding capacity of these polypeptides The polynucleotide given in FIG. 4 (nucleotides 1–710) that codes for birch P14 was inserted in the plasmid pKK223-3 so that a recombinant nonfusion protein (31) could be prepared, while a recombinant fusion protein was produced in the plasmid pEXB (32). The reactivity of these polypeptides with patient IgE is shown in FIG. 6. Control protein extracts of *E. coli* in lanes 1, 2, 5 and 6 do not bind IgE, while recombinant birch P14 expressed as a nonfusion protein (lanes 3 and 4) and as a fusion protein (lanes 7 and 8) does bind IgE.

In FIG. 7, sera from persons allergic to birch pollen (A-K), to grass pollen (L-N) and to mugwort (O-Q) and of a pool of nonallergic individuals (R), all of whom had been selected according to their case history, RAST and skin test, were tested for their IgE-binding capacity with recombinant birch P14. IgEs of Sera D, E, F, I, J and P bound to P14 expressed in pKK223-3.

It follows from this that this invention provides a polynucleotide that codes for polypeptides which have similar antigenicity and similar IgE-binding capacity to the P14 protein of birch when the polynucleotide is inserted in the correct reading frame of a variety of expression systems. The IgE-binding properties of these polypeptides were demonstrated for sera from patients who exhibit allergic reactions to various pollens and hence point to the great clinical significance of these polypeptides (FIG. 7).

5.10. Purification of P14 from pollen and of recombinant P14 from *E. coli*

As described above, this invention provides a simple method for purifying natural as well as recombinant P14. The Coomassie-stained polyacrylamide gel in FIG. 8 shows that pure P14 (lanes 3, 4 and 5) can be separated from total pollen protein (lane 1). The proteins which do not bind to poly(L-proline)-Sepharose are also shown (lane 2). The effectiveness of this purification method was monitored by means of IgE immunoblotting (FIG. 9), and for this purpose serum from a patient who recognizes most birch pollen allergens with IgE antibodies (lane 1) was used. After application of the affinity method, almost no P14 can be found (lane 2), while purified P14 was obtained in lanes 3, 4 and 5.

FIG. 10 shows a polyacrylamide gel which demonstrates the purification of recombinant P14 from *E. coli* JM105 that is transformed with the plasmid pKK223-3, which carries the P14 coding sequence. Recombinant P14 (lanes 3 and 4) was purified from the total proteins by affinity chromatography to poly(n-proline) sepharose (lane 1), the remaining proteins being shown by lane 2. FIG. 11 shows that no homologous protein from *E. coli* JM105 transformed with pKK223-3 without insert is obtained by means of the method used.

As FIGS. 9, 6 and 7 show, the purified protein (from birch and *E. coli*) retains its IgE-binding capacity. This example thus shows that the present invention likewise provides a simple and rapid purification method for P14 both as natural and recombinant polypeptide. Using poly(L-proline) to purify, both natural and recombinant P14 retain their antigenicity and IgE binding capacity. In addition, the method offers the opportunity to immobilize (and separate by affinity means) the immunologically active polypeptide.

5.11. IgE reactivity of allergic and atopic patients with human profilin

Various patient sera were selected as follows (FIG. 12): Patient 1 shows IgE antibodies which are directed against most birch pollen allergens, including BetvI and P14, patient 2 shows IgE binding only with P14 and patient 3 only with BetvI. Patient 4 is a person allergic to house dust mite and the serum pool 5 was made up of nonallergic individuals. Strip 6 is the buffer control. All these sera were tested for their IgE-binding capacity with nonrecombinant and recombinant P14 and human profilin. Those patients (FIG. 12), who recognized the nonrecombinant P14 from birch as well as the recombinant P14 from *E. coli*, also had IgE antibodies against human profilin. For this reason, this invention for the first time gives indications on the molecular level that autoimmune mechanisms might play a role in atopic and allergic diseases. Since patients with other autoimmune diseases form antibodies against P14, this invention should provide a diagnostic marker for these diseases.

5.12. Correlation of case histories of atopic and allergic patients with the binding of IgE antibodies to P14

The case histories of patients who form IgE antibodies against P14 show that all of them suffer from severe allergic symptoms which are caused by a great variety of allergens (tree and grass pollen, mite, cat and dog allergens), that they have an elevated total IgE level and show an unsatisfactory course in hyposensitization therapy. It follows from this that a positive reaction of the serum IgE of patients with P14 is usable as a good marker for the differentiation of certain groups of atopic and allergic patients. 5. 13. Demonstration of common IgE-epitopes between profilins in food (celery) and pollen P14 allergen (birch)

The IgE-inhibition experiment shown in FIG. 13 shows that there is common IgE-binding capacity of proteins homologous to the P14 allergen in pollens and food. Purified recombinant birch profilin, when added to the patients' serum in the fluid phase before the serum is incubated with the nitrocellulose bound celery profilin, is able to completely block the binding of patients' IgE to celery profilin. This indicates that the P14 allergen of birch (birch profilin) contains all IgE epitopes that can be found in celery profilin. Recombinant birch P14 allergen is therefore suitable not only for diagnosis and therapy of pollen allergies but also for food allergies.

Common antigenicity of birch pollen P14 allergen and food profilins is also shown by crossreactivity of a rabbit anti celery profilin antibody with the pollen P14 allergen (FIGS. 14 and 15).

5. 14. Sequence similarity and common IgE-binding capacity of pollen P14 allergen from white birch (*Betula verrucosa*) and the homologous P14(T) allergen from timothy grass (*Phleum pratense*).

Amino acid sequence identity of birch P14 allergen and timothy grass P14(T) allergen is 77%. The cDNA encoding the P14(T) allergen from timothy grass was obtained by screening a cDNA library, which was constructed from pollen of timothy grass in the same way as described for the cDNA library from birch pollen, with patients' IgE as described for the P14 allergen of birch. The cDNA sequence of the clone encoding the P14(T) allergen of timothy grass is shown in FIG. 16. and as sequences 9–11 in the sequence listing. All patients' sera that bound with their IgE to birch profilin also bound with their IgE to sectors of nitrocellulose filters containing plaquelifts of immunopositive lambda gt11 phages into which the cDNA encoding timothy grass P14(T) allergen had been inserted (FIG. 17). This shows that the proteins related to the P14 allergens by high homology also are immunologically cross reactive with patients' IgE antibodies.

6. METHODS OF ADMINISTRATION

The present invention covers the use of P14 synthetic polypeptide allergens to hyposensitize or desensitize a mammal. Such polypeptides can be administered to a human subject either alone or in combination with pharmaceutically acceptable carriers or diluents, in accordance with standard pharmaceutical practice.

The method of hyposensitization involves or could involve the successive parenteral, oral, nasal, inhalant or rectal administration of incremental doses of the P14 allergen. The term parenteral as used herein includes subcutaneous, intravenous or intramuscular injections.

A range from 1 picogram to 10 milligrams per application can be used. The diluents and carriers can be chosen by those skilled in the art according to commonly accepted galenic procedures.

7. REFERENCES

The references cited in the above specification are:
1. L. Yman. Botanical relations and immunological cross-reactions in pollen allergy, 2nd ed. Uppsala, Sweden: Pharmacia AB, 1982.
2. W. R. Thomas, K. Y. Chua, W. K. Greene and G. A. Stewart. Recombinant mite allergens. In: Epitopes of atopic allergens. A. H. Sehon, D. Kraft, and G. Kunkel (eds). UCB Institute of Allergy, Brussels 1990.
3. E. Jarolim, M. Tejkl, M. Rohac, G. Schlerka, M. Breitenbach, O. Scheiner, D. Kraft, H. Rumpold. Monoclonal antibodies against birch pollen allergens; characterization by immunoblotting and use for single step affinity purification of the major allergen BetvI. Int. Arch. Allergy Appl. Immunol. 90, 54–60 (1989).
4. H. Ipsen, H. Bowadt, H. Janniche, B. Nüchel Petersen, E. P. Munch, J. A. Wihl and H. Lowenstein. Immunochemical characterization of reference alder (Alnus glutinosa) and hazel (Corylus avellana) pollen extracts and the partial immunochemical identity between the major allergens of alder, birch, and hazel pollen. Allergy 40, 510–518 (1985).
5. H. Rumpold, M. Rohac, B. Bohle, M. Breitenbach, O. Scheiner and D. Kraft. The relationship of BetvI epitopes recognized by patients' IgE and monoclonal anti-BetvI antibodies. In: Epitopes of atopic allergens. A. Sehon, D. Kraft and G. Kunkel (eds). The UCB Institute of Allergy, Brussels 1990.
6. R. Valenta, H. Breiteneder, K. Pettenburger, M. Breitenbach, H. Rumpold, D. Kraft and O. Scheiner. Homology of the major pollen allergens of alder, hazel, and hornbeam at the nucleic acid level as determined by cross-hybridization. J. Allergy Clin. Immunol., in press.
7. B. Nüchel Petersen, H. Janniche, E. P. Munch, J. A. Wihl, H. Böwadt, H. Ipsen and H. Lowenstein. Immunotherapy with partially purified and standardized tree pollen extracts. Allergy 43, 353–362 (1988).
8. J. A. Wihl, H. Ipsen, B. Nüchel Petersen, E. P. Munch, H. Janniche and H. Lowenstein. Immunotherapy with partially purified tree pollen extracts. Allergy43, 363–369 (1988).
9. H. Ipsen, B. Schwartz, J. A. Wihl, B. Nüchel Petersen, E. P. Munch, H. Janniche and H. Lowenstein. Immunotherapy with partially purified and standardized tree pollen extracts. Allergy 43, 370–377 (1988).
10. C. Ampe, J. Vandekerckhove, S. L. Brenner, L. Tobacman and E. D. Korn. The amino acid sequence of Acanthamoeba profilin. J. Biol. Chem. 260, 834–840 (1985).
11. V. Magdolen, U. Oechsner, G. Müller and W. Bandlow. The intron-containing gens for yeast profilin (PFY) encodes a vital function. Mol. Cell. Biol. 8, 5108–5115 (1988).
12. J. S. Widada, C. Ferraz and J.-P. Liautard. Total coding sequence of profilin cDNA from *Mus musculus* macrophage. Nucl. Acids Res. 17, 2855 (1989).
13. D. J. Kwiatkowski and G. A. P. Bruns. Human profilin. Molecular cloning, sequence comparison, and chromosomal analysis. J. Biol. Chem. 263, 5910–5915 (1988).
14. C. Ampe, F. Markey, U. Lindberg and J. Vandekerckhove. The primary structure of human platelet profilin: reinvestigation of the calf spleen profilin sequence. FEBS Lett. 228, 17–21 (1988).
15. Lindberg, C. E. Schutt, E. Hellsten, A.-C. Tjäder und T. Hult. The use of poly(L-proline)-Sepharose in the isolation of profilin and profilactin complexes. Biochim. Biophys. Acta 967, 391–400 (1988).
16. M. Tanaka and H. Shibata. Poly(L-proline)-binding proteins from chick embryos are a profilin and a profilactin. Eur. J. Biochem. 151, 291–297 (1985).
17. H. Breiteneder, W. Hassfeld, K. Pettenburger, E. Jarolim, M. Breitenbach, H. Rumpold, D. Kraft and O. Scheiner. Isolation and characterization of messenger RNA from male inflorescences and pollen of white birch (*Betula verrucosa*). Int. Arch. Allergy Appl. Immunol. 87, 19–24 (1988).
18. H. Aviv und P. Leder. Purification of biologically active globin messenger RNA by chromatography on oligothymidylic acid-cellulose. Proc. Natl. Acad. Sci. U.S.A. 69, 1408–1412 (1972).
19. T. V. Huynh, R. A. Young, R. W. Davis, In: DNA cloning—a practical approach, Band 1, D. M. Glover (ed), IRL Press, Oxford 1985.
20. H. Haymerle. Nucl. Acids Res. 14, 8615 (1986).
21. R. A. Young and R. W. Davis. Efficient isolation of genes by using antibody probes. Proc. Natl. Acad. Sci. U.S.A. 80, 1184–1198 (1983).
22. H. Breiteneder, K. Pettenburger, A. Bito, R. Valenta, D. Kraft, H. Rumpold, O. Scheiner and M. Breitenbach. The gene coding for the major birch pollen allergen BetvI is highly homologous to a pea disease resistance response gene. EMBO J. 8, 1935–1938 (1989).
23. F. M. Ausubel. Current protocols in molecular biology. Green Publishing Associates and Wiley-Interscience, New York, 1987.
24. C. Yanisch-Perron, J. Vieira and J. Messing. Improved M13 phage cloning vectors and host strains: nucleotide sequences of the M13mp18 and pUC19 vectors. Gene33, 103–119 (1985).
25. F. Sanger, S. Nicklen and A. R. Coulson. DNA sequencing with chain-terminating inhibitors. Proc. Natl. Acad. Sci. U.S.A. 74, 5463–5467 (1977).
26. R. B. Wallace, J. Shaffer, R. F. Murphy, J. Bonner, T. Hirose and K. Itakura. Hybridization of synthetic oligodeoxyribonucleotides to ΦX 174 DNA: the effect of a single base pair mismatch. Nucleic Acids Res. 6, 3543–3557 (1979).
27. P. S. Thomas. Hybridization of denatured RNA and small DNA fragments transferred to nitrocellulose. Proc. Natl. Acad. Sci. U.S.A. 77, 5201–5205 (1980).
28. H. Lehrach. RNA molecular weight determinations by gel electrophoresis under denaturing conditions: a critical reexaminaeion. Biochemistry 16, 4743–4751 (1977).
29. A. P. Feinberg and B. Vogelstein. A technique for radiolabeling DNA restriction fragments to high specific activity. Anal. Biochem. 132, 6–13 (1983).
30. J. Shine and L. Dalgarno. The 3'-terminal sequence of *Escherichia coli* 16S ribosomal RNA: complementarity to nonsense triplets and ribosome binding sites. Proc. Natl. Acad. Sci. U.S.A. 71, 1342–1346 (1974).
31. E. Amann, J. Brosius and M. Ptashne. Vectors bearing a hybrid trp-lac promoter useful for regulated expression of cloned genes in *Eschertchia coli*. Gene 25, 167–178 (1983).
32. N. Kiyoshi, H. C. Thogersen. Generation of β-globin by sequence-specific proteolysis of a hybrid protein produced in *Escherichia coli*. Nature 309, 810–812 (1984).

33. D. M. Helfman, J. R. Feramisco, J. C. Fiddes, G. P. Thomas and S. H. Hughes. Identification of clones that encode chicken tropomyosin by direct immunological screening of a cDNA expression library. Proc. Natl. Acad. Sci. U.S.A. 80, 31–35 (1983).

What is claimed is:

1. A method for producing a P14 allergen comprising culturing a host cell transformed with a replicable expression vehicle capable of directing expression of a DNA molecule encoding the amino acid sequence of SEQ ID NO:3.

2. A method for producing a P14 allergen comprising culturing a host cell transformed with a replicable expression vehicle capable of directing expression of a DNA molecule having the nucleic acid sequence of SEQ ID NO:1.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 700 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Betula verrucosa ( v i i ) IMMEDIATE SOURCE:
        ( A ) LIBRARY: POLLEN FROM ALLERGON AB, ENGELHOLM, SWEDEN ( x i ) SEQUENCE DESCRIPTION: SEQ ID NO:1:

```
CAGAGAAAGC GAAAGCTCTC CGCCACAACA AAACGAAGTA GAAGAAGAAG AGTGAGCAAG      60
AGACAGAGGG AAGAGGAAAA TGTCGTGGCA AACGTACGTG GATGAACATT TGATGTGCGA     120
TATCGACGGG CAAGCCAGCA ACTCGCTGGC ATCTGCGATC GTCGGTCACG ATGGCTCTGT     180
GTGGGCCCAG AGCTCTTCCT TCCCACAGTT TAAGCCTCAG GAAATCACTG GTATCATGAA     240
GGACTTTGAG GAGCCGGGTC ATCTTGCTCC GACGGGCTTA CACCTTGGGG GCATAAAATA     300
CATGGTCATC CAGGGAGAGG CTGGTGCTGT CATCCGTGGA AAGAAGGGAT CTGGAGGTAT     360
TACTATAAAG AAGACTGGTC AAGCTCTCGT TTTTGGCATC TATGAAGAGC CTGTGACACC     420
AGGACAGTGC AACATGGTTG TTGAGAGGTT GGGGGATTAC CTTATTGACC AGGGCCTGTA     480
GGCAAAGGTC TATCATCATT TGGGGCTTAA TTGTTTTTTT TTTTTTTTG CTCTTATTCC      540
CTTTGATTTC GGTTCCAAGT GTGCATCGAT CTTCATTTGA AAGCCTTAAA TTGGCAGTGA     600
AGTTGTTGCA GACAATAACC ATGTGAGAAC TAAAACATTT GTCTTGTGTT TGGTTGTTTG     660
AAAAAAAAAA AAAAAAAAA AAAAAAAAA AAAAAAAAA                              700
```

( 2 ) INFORMATION FOR SEQ ID NO:2:

( i ) SEQUENCE CHARACTERISTICS:
        ( A ) LENGTH: 398 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Betula verrucosa ( v i i ) IMMEDIATE SOURCE:
        ( A ) LIBRARY: POLLEN FROM ALLERGON AB, ENGELHOLM, SWEDEN ( x i ) SEQUENCE DESCRIPTION: SEQ ID NO:2:

| | | | | | | |
|---|---|---|---|---|---|---|
| ATGTCGTGGC | AAACGTACGT | GGATGAACAT | TTGATGTGCG | ATATCGACGG | GCAAGCCAGC | 60 |
| AACTCGCTGG | CATCTGCGAT | CGTCGGTCAC | GATGGCTCTG | TGTGGGCCCA | GAGCTCTTCC | 120 |
| TTCCCACAGT | TTAAGCCTCA | GGAAATCACT | GGTATCATGA | AGGACTTTGA | GGAGCCGGGT | 180 |
| CATCTTGCTC | CGACGGGCTT | ACACCTTGGG | GGCATAAAAT | ACATGGTCAT | CCAGGGAGAG | 240 |
| GCTGGTGCTG | TCATCCGTGG | AAAGAAGGGA | TCTGGAGGTA | TTACTATAAA | GAAGACTGGT | 300 |
| CAAGCTCTCG | TTTTGGCAT | CTATGAAGAG | CCTGTGACAC | CAGGACAGTG | CAACATGGTT | 360 |
| GTTGAGAGGT | TGGGGATTA | CCTTATTGAC | CAGGGCTG | | | 398 |

( 2 ) INFORMATION FOR SEQ ID NO:3:

( i ) SEQUENCE CHARACTERISTICS:
( A ) LENGTH: 133 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( A ) ORGANISM: Betula verrucosa ( i x ) FEATURE:
( D ) OTHER INFORMATION: Amino acid sequence identity
with profilin of other organisms is as follows:
30% with human profilin, 28% with calf and mouse,
26% with yeast and 25% with Acanthamoeba ( x i ) SEQUENCE DESCRIPTION: SEQ ID NO:3:

```
Met Ser Trp Gln Thr Tyr Val Asp Glu His Leu Met Cys Asp Ile Asp
 1               5                  10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
                100                 105                 110

Thr Pro Gly Gln Cys Asn Met Val Val Glu Arg Leu Gly Asp Tyr Leu
            115                 120                 125

Ile Asp Gln Gly Leu
        130
```

( 2 ) INFORMATION FOR SEQ ID NO:4:

( i ) SEQUENCE CHARACTERISTICS:
( A ) LENGTH: 140 amino acids
( B ) TYPE: amino acid
( D ) TOPOLOGY: linear ( i i ) MOLECULE TYPE: peptide ( i i i ) HYPOTHETICAL: NO ( v i ) ORIGINAL SOURCE:
( A ) ORGANISM: Mouse (murine)

( i x ) FEATURE:
    ( D ) OTHER INFORMATION: 28% identical with the P14
        allergen of birch (Betula verrucosa)

( x ) PUBLICATION INFORMATION: Reference 12

( x i ) SEQUENCE DESCRIPTION: SEQ ID NO:4:

| Met | Ala | Gly | Trp | Asn | Ala | Tyr | Ile | Asp | Ser | Leu | Met | Ala | Asp | Gly | Thr |
| 1 | | | | 5 | | | | | 10 | | | | | 15 | |

| Cys | Gln | Asp | Ala | Ala | Ile | Val | Gly | Tyr | Lys | Asp | Ser | Pro | Ser | Val | Trp |
| | | | 20 | | | | | 25 | | | | | 30 | | |

| Ala | Ala | Val | Pro | Gly | Lys | Thr | Phe | Val | Ser | Ile | Thr | Pro | Ala | Glu | Val |
| | | 35 | | | | | 40 | | | | | 45 | | | |

| Gly | Val | Leu | Val | Gly | Lys | Asp | Arg | Ser | Ser | Phe | Phe | Val | Asn | Gly | Leu |
| | 50 | | | | | 55 | | | | | 60 | | | | |

| Thr | Leu | Gly | Gly | Gln | Lys | Cys | Ser | Val | Ile | Arg | Asp | Ser | Leu | Leu | Gln |
| 65 | | | | | 70 | | | | | 75 | | | | | 80 |

| Asp | Gly | Glu | Phe | Thr | Met | Asp | Leu | Arg | Thr | Lys | Ser | Thr | Gly | Gly | Ala |
| | | | | 85 | | | | | 90 | | | | | 95 | |

| Pro | Thr | Phe | Asn | Val | Thr | Val | Thr | Met | Thr | Ala | Lys | Thr | Leu | Val | Leu |
| | | | 100 | | | | | 105 | | | | | 110 | | |

| Leu | Met | Gly | Lys | Glu | Gly | Val | His | Gly | Gly | Leu | Ile | Asn | Lys | Lys | Cys |
| | | 115 | | | | | 120 | | | | | 125 | | | |

| Tyr | Glu | Met | Ala | Ser | His | Leu | Arg | Arg | Ser | Gln | Tyr |
| | | 130 | | | | | 135 | | | | 140 |

( 2 ) INFORMATION FOR SEQ ID NO:5:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Calf (bovine)

( i x ) FEATURE:
        ( D ) OTHER INFORMATION: 28% identical with the P14
            allergen of birch (Betula verrucosa)

( x ) PUBLICATION INFORMATION: Reference 14

( x i ) SEQUENCE DESCRIPTION: SEQ ID NO:5:

| Ala | Gly | Trp | Asn | Ala | Tyr | Ile | Asp | Asn | Leu | Met | Ala | Asp | Gly | Thr | Cys |
| 1 | | | | 5 | | | | | 10 | | | | | 15 | |

| Gln | Asp | Ala | Ala | Ile | Val | Gly | Tyr | Lys | Asp | Ser | Pro | Ser | Val | Trp | Ala |
| | | | 20 | | | | | 25 | | | | | 30 | | |

| Ala | Val | Pro | Gly | Lys | Thr | Phe | Val | Asn | Ile | Thr | Pro | Ala | Glu | Val | Gly |
| | | 35 | | | | | 40 | | | | | 45 | | | |

| Ile | Leu | Val | Gly | Lys | Asp | Arg | Ser | Ser | Phe | Phe | Val | Asn | Gly | Leu | Thr |
| | 50 | | | | | 55 | | | | | 60 | | | | |

| Leu | Gly | Gly | Gln | Lys | Cys | Ser | Val | Ile | Arg | Asp | Ser | Leu | Leu | Gln | Asp |
| 65 | | | | | 70 | | | | | 75 | | | | | 80 |

| Gly | Glu | Phe | Thr | Met | Asp | Leu | Arg | Thr | Lys | Ser | Thr | Gly | Gly | Ala | Pro |
| | | | | 85 | | | | | 90 | | | | | 95 | |

| Thr | Phe | Asn | Ile | Thr | Val | Thr | Met | Thr | Ala | Lys | Thr | Leu | Val | Leu | Leu |
| | | | 100 | | | | | 105 | | | | | 110 | | |

| | | | | | | | | | | | | | | | |
|---|---|---|---|---|---|---|---|---|---|---|---|---|---|---|---|
| Met | Gly | Lys | Gln | Gly | Val | His | Gly | Gly | Met | Ile | Asn | Lys | Lys | Cys | Tyr |
| | | 115 | | | | | 120 | | | | | 125 | | | |
| Glu | Met | Ala | Ser | His | Leu | Arg | Arg | Ser | Gln | Tyr | | | | | |
| | | 130 | | | | | 135 | | | | | | | | |

( 2 ) INFORMATION FOR SEQ ID NO:6:

( i ) SEQUENCE CHARACTERISTICS:
        ( A ) LENGTH: 140 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Human (Homo sapiens)

( i x ) FEATURE:
        ( D ) OTHER INFORMATION: 30% identical with the P14
        allergen of birch (Betula verrucosa)

( x ) PUBLICATION INFORMATION: Reference 13

( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Ala | Gly | Trp | Asn | Ala | Tyr | Ile | Asp | Asn | Leu | Met | Ala | Asp | Gly | Thr |
| 1 | | | | 5 | | | | | 10 | | | | | 15 | |
| Cys | Gln | Asp | Ala | Ala | Ile | Val | Gly | Tyr | Lys | Asp | Ser | Pro | Ser | Val | Trp |
| | | | 20 | | | | | 25 | | | | 30 | | | |
| Ala | Ala | Val | Pro | Gly | Lys | Thr | Phe | Val | Asn | Ile | Thr | Pro | Ala | Glu | Val |
| | | 35 | | | | | 40 | | | | | 45 | | | |
| Gly | Val | Leu | Val | Gly | Lys | Asp | Arg | Ser | Ser | Phe | Tyr | Val | Asn | Gly | Leu |
| | 50 | | | | | 55 | | | | | 60 | | | | |
| Thr | Leu | Gly | Gly | Gln | Lys | Cys | Ser | Val | Ile | Arg | Asp | Ser | Leu | Leu | Gln |
| 65 | | | | | 70 | | | | | 75 | | | | | 80 |
| Asp | Gly | Glu | Phe | Ser | Met | Asp | Leu | Arg | Thr | Lys | Ser | Thr | Gly | Gly | Ala |
| | | | | 85 | | | | | 90 | | | | | 95 | |
| Pro | Thr | Phe | Asn | Val | Thr | Val | Thr | Lys | Thr | Asp | Lys | Thr | Leu | Val | Leu |
| | | | 100 | | | | | 105 | | | | | 110 | | |
| Leu | Met | Gly | Lys | Glu | Gly | Val | His | Gly | Gly | Leu | Ile | Asn | Lys | Lys | Cys |
| | | 115 | | | | | 120 | | | | | 125 | | | |
| Tyr | Glu | Met | Ala | Ser | His | Leu | Arg | Arg | Ser | Gln | Tyr | | | | |
| | 130 | | | | | 135 | | | | | 140 | | | | |

( 2 ) INFORMATION FOR SEQ ID NO:7:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Yeast ( i x ) FEATURE:
        ( D ) OTHER INFORMATION: 26% identical with the P14
        allergen of birch (Betula verrucosa)

( x ) PUBLICATION INFORMATION: Reference 11

( x i ) SEQUENCE DESCRIPTION: SEQ ID NO:7:

| | | | | | | | | | | | | | | | |
|---|---|---|---|---|---|---|---|---|---|---|---|---|---|---|---|
| Met | Ser | Trp | Gln | Ala | Tyr | Thr | Asp | Asn | Leu | Ile | Gly | Thr | Gly | Lys | Val |

| | 1 | | | 5 | | | | | 10 | | | | | 15 | |
|---|---|---|---|---|---|---|---|---|---|---|---|---|---|---|---|
| | Asp | Lys | Ala | Val<br>20 | Ile | Tyr | Ser | Arg | Ala<br>25 | Gly | Asp | Ala | Val | Trp<br>30 | Ala | Thr |
| | Ser | Gly | Gly<br>35 | Leu | Ser | Leu | Gln | Pro<br>40 | Asn | Glu | Ile | Gly | Glu<br>45 | Ile | Val | Gln |
| | Gly | Phe<br>50 | Asp | Asn | Pro | Ala | Gly<br>55 | Leu | Gln | Ser | Asn | Gly<br>60 | Leu | His | Ile | Gln |
| | Gly<br>65 | Gln | Lys | Phe | Met | Leu<br>70 | Leu | Arg | Ala | Asp | Asp<br>75 | Arg | Ser | Ile | Tyr | Gly<br>80 |
| | Arg | His | Asp | Ala | Glu<br>85 | Gly | Val | Val | Cys | Val<br>90 | Arg | Thr | Lys | Gln | Thr<br>95 | Val |
| | Ile | Ile | Ala | His<br>100 | Tyr | Pro | Pro | Thr | Val<br>105 | Gln | Ala | Gly | Glu | Ala<br>110 | Thr | Lys |
| | Ile | Val | Glu<br>115 | Gln | Leu | Ala | Asp | Tyr<br>120 | Leu | Ile | Gly | Val | Gln<br>125 | Tyr | | |

( 2 ) INFORMATION FOR SEQ ID NO:8:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Acanthamoeba ( i x ) FEATURE:
        ( D ) OTHER INFORMATION: 25% identical with the P14
        allergen of birch (Betula verrucosa)

( x ) PUBLICATION INFORMATION: Reference 10

( x i ) SEQUENCE DESCRIPTION: SEQ ID NO:8:

| | Thr<br>1 | Trp | Gln | Ser | Tyr<br>5 | Val | Asp | Thr | Asn | Leu<br>10 | Val | Gly | Thr | Gly | Ala<br>15 | Val |
|---|---|---|---|---|---|---|---|---|---|---|---|---|---|---|---|---|
| | Thr | Gln | Ala | Ala<br>20 | Ile | Leu | Gly | Leu | Asp<br>25 | Gly | Asn | Thr | Trp | Ala<br>30 | Ser | Phe |
| | Ala | Gly | Phe<br>35 | Ala | Val | Thr | Pro | Ala<br>40 | Gln | Gly | Thr | Thr | Leu<br>45 | Ala | Gly | Ala |
| | Phe | Asn<br>50 | Asn | Ala | Asp | Ala | Ile<br>55 | Arg | Ala | Gly | Gly | Phe<br>60 | Asp | Leu | Ala | Gly |
| | Val<br>65 | His | Tyr | Val | Thr | Leu<br>70 | Arg | Ala | Asp | Asp | Arg<br>75 | Ser | Ile | Tyr | Gly | Lys<br>80 |
| | Lys | Gly | Ala | Ser | Gly<br>85 | Val | Ile | Thr | Val | Lys<br>90 | Thr | Ser | Lys | Ser | Ile<br>95 | Leu |
| | Val | Gly | Val | Tyr<br>100 | Asn | Glu | Lys | Ile | Gln<br>105 | Pro | Gly | Thr | Ala | Ala<br>110 | Asn | Val |
| | Val | Glu | Lys<br>115 | Leu | Ala | Asp | Tyr | Leu<br>120 | Ile | Gly | Gln | Gly | Phe<br>125 | | | |

( 2 ) INFORMATION FOR SEQ ID NO:9:

( i ) SEQUENCE CHARACTERISTICS:
        ( A ) LENGTH: 641 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (v) ORIGINAL SOURCE:
    (A) ORGANISM: Phleum pratense (vii) IMMEDIATE SOURCE:
    (A) LIBRARY: POLLEN FROM ALLERGON AB, ENGELHOLM, SWEDEN (xi) SEQUENCE DESCRIPTION: SEQ ID NO:9:

| | | | | | |
|---|---|---|---|---|---|
| GAAAGCAAAC | TTGCAGGACC | GAAGATGTCG | TGGCAGACGT | ACGTGGACGA | GCACCTGATG | 60 |
| TGCGAGATCG | AGGGCCACCA | CCTCGCCTCG | GCGGCCATCC | TCGGCCACGA | CGGCACCGTC | 120 |
| TGGGCCCAGA | GCGCCGACTT | CCCCCAGTTC | AAGCCTGAGG | AGATCACCGG | CATCATGAAG | 180 |
| GATTTCGACG | AGCCGGGGCA | CCTCGCCCCC | ACCGGCATGT | TCGTCGCAGG | TGCCAAGTAC | 240 |
| ATGGTCATCC | AGGGTGAACC | CGGTCGCGTC | ATCCGTGGCA | AGAAGGGAGC | AGGAGGCATC | 300 |
| ACCATAAAGA | AGACCGGGCA | GGCGCTGGTC | GTCGGCATCT | ATGACGAGCC | CATGACCCCT | 360 |
| GGGCAGTGCA | ACATGGTGGT | GGAGAGGCTT | GGCGACTACC | TCGTTGAACA | AGGCATGTAG | 420 |
| ACTGGCTGAT | CCATGGCTTC | CACGTCTCCA | CGATCGATGA | TGATCATACA | GTTTTCACG | 480 |
| TTCTTTTAAA | CATCTATTGG | AATATATATG | GGCTTCTCC | TCTTTTACCG | GCTCTGGTCA | 540 |
| TGGATCACTG | ATGACCAGTT | GCTCTGGAAG | TTTCATTTGT | AATGCCATCT | TGGCTTTCTA | 600 |
| TCTTCTTCAA | TGTTTTTTTT | TTCTTTCGG | TTAAAAAAAA | A | | 641 |

(2) INFORMATION FOR SEQ ID NO:10:

(i) SEQUENCE CHARACTERISTICS:
        (A) LENGTH: 393 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) ORIGINAL SOURCE:
        (A) ORGANISM: Phleum pratense (vii) IMMEDIATE SOURCE:
        (A) LIBRARY: POLLEN FROM ALLERGON AB, ENGELHOLM, SWEDEN (xi) SEQUENCE DESCRIPTION: SEQ ID NO:10:

| | | | | | |
|---|---|---|---|---|---|
| ATGTCGTGGC | AGACGTACGT | GGACGAGCAC | CTGATGTGCG | AGATCGAGGG | CCACCACCTC | 60 |
| GCCTCGGCGG | CCATCCTCGG | CCACGACGGC | ACCGTCTGGG | CCCAGAGCGC | CGACTTCCCC | 120 |
| CAGTTCAAGC | CTGAGGAGAT | CACCGGCATC | ATGAAGGATT | TCGACGAGCC | GGGGCACCTC | 180 |
| GCCCCCACCG | GCATGTTCGT | CGCAGGTGCC | AAGTACATGG | TCATCCAGGG | TGAACCCGGT | 240 |
| CGCGTCATCC | GTGGCAAGAA | GGGAGCAGGA | GGCATCACCA | TAAAGAAGAC | CGGGCAGGCG | 300 |
| CTGGTCGTCG | GCATCTATGA | CGAGCCCATG | ACCCCTGGGC | AGTGCAACAT | GGTGGTGGAG | 360 |
| AGGCTTGGCG | ACTACCTCGT | TGAACAAGGC | ATG | | | 393 |

(2) INFORMATION FOR SEQ ID NO:11:

(i) SEQUENCE CHARACTERISTICS:
        (A) LENGTH: 131 amino acids
        (B) TYPE: amino acid
        (D) TOPOLOGY: linear ( i i ) MOLECULE TYPE: peptide ( i i i ) HYPOTHETICAL: NO ( v i ) ORIGINAL SOURCE:
    ( A ) ORGANISM: Phleum pratense ( i x ) FEATURE:
    ( D ) OTHER INFORMATION: Amino acid identity with P14
        allergen from Betula verrucosa is 77%

( x i ) SEQUENCE DESCRIPTION: SEQ ID NO:11:

```
Met Ser Trp Gln Thr Tyr Val Asp Glu His Leu Met Cys Glu Ile Glu
 1               5                  10                     15

Gly His His Leu Ala Ser Ala Ala Ile Leu Gly His Asp Gly Thr Val
             20                  25                 30

Trp Ala Gln Ser Ala Asp Phe Pro Gln Ile Lys Pro Glu Glu Ile Thr
         35              40                  45

Gly Ile Met Lys Asp Phe Asp Glu Pro Gly His Leu Ala Pro Thr Gly
     50              55                  60

Met Phe Val Ala Gly Ala Lys Tyr Met Val Ile Gln Gly Glu Pro Gly
 65              70                  75                     80

Arg Val Ile Arg Gly Lys Lys Gly Ala Gly Gly Ile Thr Ile Lys Lys
             85                  90                     95

Thr Gly Gln Ala Leu Val Val Gly Ile Tyr Asp Glu Pro Met Thr Pro
            100              105                 110

Gly Gln Cys Asn Met Val Val Glu Arg Leu Gly Asp Tyr Leu Val Glu
            115              120                 125

Gln Gly Met
    130
```